(12) United States Patent
Fu et al.

(10) Patent No.: US 11,865,370 B2
(45) Date of Patent: Jan. 9, 2024

(54) SYSTEMS AND METHODS FOR CONTROLLING RADIATION OUTPUT

(71) Applicant: SHANGHAI UNITED IMAGING HEALTHCARE CO., LTD., Shanghai (CN)

(72) Inventors: Feichao Fu, Shanghai (CN); Xing Xu, Shanghai (CN); Zhou Xue, Shanghai (CN); Johannes Stahl, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 258 days.

(21) Appl. No.: 17/305,516

(22) Filed: Jul. 9, 2021

(65) Prior Publication Data
US 2021/0339051 A1 Nov. 4, 2021

Related U.S. Application Data

(63) Continuation of application No. PCT/CN2020/070068, filed on Jan. 2, 2020.

(51) Int. Cl.
*A61N 5/10* (2006.01)

(52) U.S. Cl.
CPC ......... *A61N 5/1077* (2013.01); *A61N 5/1044* (2013.01); *A61N 5/1071* (2013.01); *A61N 2005/1074* (2013.01); *A61N 2005/1089* (2013.01)

(58) Field of Classification Search
None
See application file for complete search history.

(56) References Cited

U.S. PATENT DOCUMENTS

| | | | |
|---|---|---|---|
| 8,604,723 B2 | 12/2013 | Chen et al. | |
| 8,942,351 B2 | 1/2015 | Cheung et al. | |
| 2007/0014392 A1 | 1/2007 | Madey et al. | |
| 2008/0043910 A1 | 2/2008 | Thomas | |
| 2010/0014097 A1 | 1/2010 | Sogard | |
| 2010/0081971 A1* | 4/2010 | Allison | A61F 7/00 606/1 |
| 2014/0022114 A1 | 1/2014 | Kamimura et al. | |
| 2014/0046407 A1 | 2/2014 | Ben-Ezra et al. | |

(Continued)

OTHER PUBLICATIONS

International Search Report in PCT/CN2020/070068 dated Sep. 28, 2020, 4 pages.

(Continued)

*Primary Examiner* — Hoon K Song
(74) *Attorney, Agent, or Firm* — METIS IP LLC

(57) ABSTRACT

A method may include identifying a time window of a procedure. The method may also include obtaining operational information of the time window. The operational information may include a limit of pulse repetition frequency (PRF) acceleration and a plurality of preliminary radio frequency (RF) PRFs. The method may also include determining a plurality of updated RF PRFs by updating the plurality of preliminary RF PRFs. A rate of variation between any two adjacent updated RF PRFs may be less than or equal to the limit of PRF acceleration. The method may also include causing an RF source to generate electromagnetic waves at the plurality of updated RF PRFs in the time window.

20 Claims, 17 Drawing Sheets

(56) References Cited

U.S. PATENT DOCUMENTS

| | | |
|---|---|---|
| 2015/0297188 A1* | 10/2015 | Konofagou .............. A61B 8/08 |
| | | 600/442 |
| 2015/0378003 A1 | 12/2015 | Mayer |
| 2016/0011300 A1 | 1/2016 | Lee |
| 2016/0259032 A1 | 9/2016 | Hehn et al. |
| 2016/0302075 A1 | 10/2016 | Dudda et al. |
| 2018/0149756 A1 | 5/2018 | Yang et al. |
| 2019/0060669 A1 | 2/2019 | Stahl et al. |
| 2019/0209864 A1* | 7/2019 | Stahl ................... A61N 5/1045 |

OTHER PUBLICATIONS

Written Opinion in PCT/CN2020/070068 dated Sep. 28, 2020, 4 Pages.
First Office Action in Chinese Application No. 202080003837.5 dated Jun. 2, 2022, 12 pages.

* cited by examiner

SYSTEMS AND METHODS FOR CONTROLLING RADIATION OUTPUT

CROSS-REFERENCE OF RELATED APPLICATIONS

This application is Continuation of International Application No. PCT/CN2020/070068, filed on Jan. 2, 2020, the contents of which are hereby incorporated by reference.

TECHNICAL FIELD

The present disclosure generally relates to radiation generation, and more particularly, to systems and methods for configuring electromagnetic waves that are applied for electron acceleration in radiation generation.

BACKGROUND

In radiation beam delivery, such as radiotherapy, an acceleration structure is configured to provide radiation pulses delivered to an object at a radiation PRF. An electron gun is configured to inject electrons into the acceleration structure at an electron RPF. A radio frequency (RF) source is configured to inject electromagnetic waves into the acceleration structure at an RF pulse repetition frequency (PRF) to accelerate the electrons, thereby generating radiation pulses. In general, the radiation PRF may correspond to the RF PRF. In this way, however, there may be a case in which a difference between two neighboring RF PRFs is relatively large so that there may be an abrupt output change when the RF source outputs electromagnetic waves at the two neighboring RF PRFs, which reduces the stability of the RF source. Therefore, it is desirable to provide systems and/or methods for configuring electromagnetic waves that are applied for electron acceleration in radiation generation to improve the stability of the RF source.

SUMMARY

According to a first aspect of the present disclosure, a system may include one or more storage media and one or more processors configured to communicate with the one or more storage media. The one or more storage media may include a set of instructions. When the one or more processors executing the set of instructions, the one or more processors may be directed to perform one or more of the following operations. The one or more processors may identify a time window of a procedure. The one or more processors may obtain operational information of the time window. The operational information may include a limit of pulse repetition frequency (PRF) acceleration and a plurality of preliminary radio frequency (RF) PRFs. The one or more processors may determine a plurality of updated RF PRFs by updating the plurality of preliminary RF PRFs. A rate of variation between any two adjacent updated RF PRFs may be less than or equal to the limit of PRF acceleration. The one or more processors may cause an RF source to generate electromagnetic waves at the plurality of updated RF PRFs in the time window.

In some embodiments, to determine the plurality of updated RF PRFs by updating the plurality of preliminary RF PRFs, the one or more processors may divide the forward window into a plurality of segments. In each of the plurality of segments, the one or more processors may designate a maximum preliminary RF PRF within the segment as a segment PRF of the segment. The one or more processors may determine the plurality of updated RF PRFs by joining, based on the segment PRFs of the plurality of segments, any two adjacent segments of the plurality of segments with a bridging PRF acceleration that is lower than or equal to the limit of PRF acceleration.

In some embodiments, the operational information of the time window may further include a minimum duration of an RF PRF.

In some embodiments, to determine the plurality of updated RF PRFs by joining any two adjacent segments of the plurality of segments with the bridging PRF acceleration that is lower than or equal to the limit of PRF acceleration, the one or more processors may identify one or more valley segments from the plurality of segments, wherein for each of the one or more valley segments, the segment PRF of the valley segment may be less than the segment PRFs of valley adjacent segments of the valley segment. The valley adjacent segments and the valley segment may be three consecutive segments in the forward window with the valley segment in the middle. The one or more processors may process the one or more valley segments based on the one or more segment PRFs corresponding to the one or more valley segments, the limit of PRF acceleration, and the minimum duration of an RF PRF. The one or more processors may identify one or more intermediate segments from the plurality of segments, wherein for each of the one or more intermediate segments, the segment PRF of the intermediate segment may be less than the segment PRF of only one of one or more intermediate adjacent segments of the intermediate segment. The one or more intermediate adjacent segments and the intermediate segment may be three consecutive segments in the forward window with the intermediate segment in the middle or two consecutive segments in the forward window. The one or more processors may process the one or more intermediate segments based on the one or more segment PRFs of the one or more intermediate segments, the limit of PRF acceleration, and the minimum duration of an RF PRF. The one or more processors may determine a plurality of envelopes based on the one or more processed valley segments and the one or more processed intermediate segments. The one or more processors may determine the plurality of updated RF PRFs by joining any two adjacent envelopes of the plurality of envelopes with the bridging PRF acceleration that is lower than or equal to the limit of PRF acceleration.

In some embodiments, to process the one or more valley segments based on the one or more segment PRFs corresponding to the one or more valley segments, the limit of PRF acceleration, and the minimum duration of an RF PRF, the one or more processors may determine, for each of the one or more valley segments, a first sum of a de-acceleration time of the valley segment, an acceleration time of the valley segment, and the minimum duration of an RF PRF. The one or more processors may determine whether the first sum is shorter than a segment time of the valley segment. In response to a determination that the first sum is shorter than the segment time of the valley segment, the one or more processors may retain the valley segment. In response to a determination that the first sum is longer than the segment time of the valley segment, the one or more processors may merge the valley segment with a first adjacent segment of the valley adjacent segments by increasing the segment PRF of the valley segment to the segment PRF of the first adjacent segment. The segment PRF of the first adjacent segment may be less than the segment RPF of a second adjacent segment of the valley adjacent segments.

In some embodiments, to process the one or more valley segments based on the one or more segment PRFs corresponding to the one or more valley segments, the limit of PRF acceleration, and the minimum duration of an RF PRF, for each of the one or more valley segments, the one or more processors may determine a first difference between the segment PRF of the segment prior to the valley segment and the segment PRF of the valley segment. The one or more processors may determine the de-acceleration time based on the first difference and the limit of PRF acceleration. The one or more processors may determine a second difference between the segment PRF of the segment immediately following the valley segment and the segment PRF of the valley segment. The one or more processors may determine the acceleration time based on the second difference and the limit of PRF acceleration.

In some embodiments, to process the one or more intermediate segments based on the one or more segment PRFs corresponding to the one or more intermediate segments, the limit of PRF acceleration, and the minimum duration of an RF PRF, for each of the one or more intermediate segments, the one or more processors may determine a second sum of a de-acceleration time or an acceleration time of the intermediate segment plus the minimum duration of an RF PRF. The one or more processors may determine whether the second sum is shorter than a segment time of the intermediate segment. In response to a determination that the second sum is shorter than the segment time of the intermediate segment, the one or more processors may retain the intermediate segment. In response to a determination that the second sum is longer than the segment time of the intermediate segment, the one or more processors may merge the intermediate segment with a third adjacent segment of the one or more intermediate adjacent segments by increasing the segment PRF of the intermediate segment to the segment PRF of the third adjacent segment. The segment PRF of the third adjacent segment may be larger than the segment RPF of the intermediate segment.

In some embodiments, to process the one or more intermediate segments based on the one or more segment PRFs corresponding to the one or more intermediate segments, the limit of PRF acceleration, and the minimum duration of an RF PRF, for each of the one or more intermediate segments, the one or more processors may determine a third difference between the segment PRF of the third adjacent segment and the segment PRF of the intermediate segment. The one or more processors may determine the de-acceleration time or the acceleration time based on the third difference and the limit of PRF acceleration.

In some embodiments, the time window may include a start and an end. To determine the plurality of updated RF PRFs by joining any two adjacent segments of the plurality of segments with the bridging PRF acceleration that is lower than or equal to the limit of PRF acceleration, the one or more processors may identify, from the start to the end of the time window, one or more descending segments from the plurality of segments based on the segment PRFs of the plurality of segments, wherein for each of the one or more descending segments, the segment PRF of the descending segment is less than the segment PRF of the segment prior to the descending segment. The one or more processors may process the one or more descending segments based on the one or more segment PRFs of the one or more descending segments and the limit of PRF acceleration. The one or more processors may identify, from the end to the start of the time window, one or more ascending segments from the plurality of segments based on the segment PRFs of the plurality of segments and the one or more processed descending segments, wherein for each of the one or more ascending segments, the segment PRF of the ascending segment is less than the segment PRF of the segment immediately following the ascending segment. The one or more processors may process the one or more ascending segments based on the one or more segment PRFs of the one or more ascending segments and the limit of PRF acceleration. The one or more processors may determine a plurality of envelopes based on the one or more processed descending segments and the one or more processed ascending segments. The one or more processors may determine the plurality of updated RF PRFs by joining any two adjacent envelopes of the plurality of envelopes with the bridging PRF acceleration that is lower than or equal to the limit of PRF acceleration.

In some embodiments, to process the one or more descending segments based on the one or more segment PRFs of the one or more descending segments and the limit of PRF acceleration, for each of the one or more descending segments, the one or more processors may determine a descending PRF based on the limit of PRF acceleration and the segment PRF of the segment prior to the descending segment, wherein the descending PRF refers to a value that the segment PRF of the segment prior to the descending segment decreases to at a rate of the limit of PRF acceleration from a start to an end of the descending segment. The one or more processors may determine whether the descending PRF is less than the segment PRF of the descending segment. In response to a determination that the descending PRF is less than the segment PRF of the descending segment, the one or more processors may retain the descending segment. In response to a determination that the descending PRF is larger than the segment PRF of the descending segment, the one or more processors may replace the segment PRF of the descending segment with the descending segment.

In some embodiments, to process the one or more ascending segments based on the one or more segment PRFs of the one or more ascending segments and the limit of PRF acceleration, for each of the one or more ascending segments, the one or more processors may determine an ascending PRF based on the limit of PRF acceleration and the segment PRF of the segment immediately following the ascending segment, wherein the ascending PRF refers to a value that the segment PRF of the segment immediately following the ascending segment decreases to at a rate of the limit of PRF acceleration from an end to a start of the ascending segment. The one or more processors may determine whether the ascending PRF is less than the segment PRF of the descending segment. In response to a determination that the ascending PRF is less than the segment PRF of the ascending segment, the one or more processors may retain the ascending segment. In response to a determination that the ascending PRF is larger than the segment PRF of the ascending segment, the one or more processors may replace the segment PRF of the ascending segment with the ascending PRF.

In some embodiments, the procedure may be a treatment by radiation. The time window of the procedure may be a forward window corresponding to at least a portion of a treatment that has not been performed.

According to another aspect of the present disclosure, a method may include one or more of the following operations. One or more processors may identify a time window of a procedure. The one or more processors may obtain operational information of the time window. The operational information may include a limit of pulse repetition frequency (PRF) acceleration and a plurality of preliminary radio frequency (RF) PRFs. The one or more processors may determine a plurality of updated RF PRFs by updating the plurality of preliminary RF PRFs. A rate of variation between any two adjacent updated RF PRFs may be less than or equal to the limit of PRF acceleration. The one or more processors may cause an RF source to generate electromagnetic waves at the plurality of updated RF PRFs in the time window.

According to yet another aspect of the present disclosure, a system may include a first window obtaining unit configured to identify a time window of a procedure. The system may also include a first information obtaining unit configured to obtain operational information of the time window. The operational information may include a limit of pulse repetition frequency (PRF) acceleration and a plurality of preliminary radio frequency (RF) PRFs. The system may also include an updating unit configured to determine a plurality of updated RF PRFs by updating the plurality of preliminary RF PRFs. A rate of variation between any two adjacent updated RF PRFs may be less than or equal to the limit of PRF acceleration. The system may also include a first control unit configured to cause an RF source to generate electromagnetic waves at the plurality of updated RF PRFs in the time window.

According to yet another aspect of the present disclosure, a non-transitory computer readable medium may comprise at least one set of instructions. The at least one set of instructions may be executed by one or more processors of a computer device. The one or more processors may identify a time window of a procedure. The one or more processors may obtain operational information of the time window. The operational information may include a limit of pulse repetition frequency (PRF) acceleration and a plurality of preliminary radio frequency (RF) PRFs. The one or more processors may determine a plurality of updated RF PRFs by updating the plurality of preliminary RF PRFs. A rate of variation between any two adjacent updated RF PRFs may be less than or equal to the limit of PRF acceleration. The one or more processors may cause an RF source to generate electromagnetic waves at the plurality of updated RF PRFs in the time window.

According to yet another aspect of the present disclosure, a system for controlling radiation output may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a forward window. The forward window may be at least a portion of a treatment plan that has not been performed. The one or more processors may obtain forward information of the forward window. The forward information may include time information of the forward window, a target dose relating to the forward window, and a dose per pulse (DPP) relating to the forward window. The one or more processors may determine a pulse repetition frequency (PRF) of the forward window based on the DPP, the target dose, and the time information of the forward window. The one or more processors may obtain a pulse sequence pattern, wherein the pulse sequence pattern includes a plurality of pulse sequences during a period of time. Each of the plurality of pulse sequences may correspond to a specific PRF. Each of the plurality of pulse sequences may include a plurality of pulses and a generation time of each of the plurality of pulses. The one or more processors may select a portion of the pulse sequence pattern based on the time information of the forward window and the determined PRF of the forward window. The one or more processors may cause a radiation device to deliver one or more radiation pulses to an object according to the selected portion of the pulse sequence pattern.

In some embodiments, to cause the radiation device to deliver the one or more pulses to the object according to the selected portion of the pulse sequence pattern, the one or more processors may cause, based on the selected portion of the pulse sequence pattern, an electron gun of the radiation device to inject electrons into an acceleration structure of the radiation device at an electron frequency. The one or more processors may cause, based on the selected portion of the pulse sequence pattern, an RF source of the radiation device to inject electromagnetic waves into the acceleration structure at an RF PRF. The one or more processors may cause the acceleration structure to deliver, based on the injected electrons and the electromagnetic waves, the one or more radiation pulses to the object.

In some embodiments, a difference between the RF PRF and a prior PF PRF that have been performed by the RF source may be less than a threshold.

In some embodiments, to select the portion of the pulse sequence pattern based on the time information of the forward window and the determined PRF of the forward window, the one or more processors may determine whether the determined PRF is less than a PRF threshold. In response to a determination that the determined PRF is greater than the PRF threshold, the one or more processors may select a first portion of the pulse sequence pattern, the first portion corresponding to the time information of the forward window and the determined PRF of the forward window. In response to a determination that the determined PRF is less than the PRF threshold, the one or more processors may select a second portion of the pulse sequence pattern. The second portion may correspond to the time information of the forward window and the PRF threshold.

In some embodiments, to cause the radiation device to deliver the one or more radiation pulses to the object according to the selected portion of the pulse sequence pattern, the one or more processors may determine a first count of radiation pulses based on the target dose and the DPP. The one or more processors may compare the first count of pulses to 0 and a second count of pulses in the selected portion of the pulse sequence pattern. In response to a determination that the first count of pulses is less than 0, the one or more processors may cause the acceleration structure to deliver no pulse to the object. In response to a determination that the first count of pulses is larger than the second count of pulses, the one or more processors may cause the acceleration structure to deliver the one or more pulses to the object according to the selected portion of the pulse sequence pattern. In response to a determination that the first count of pulses is between 0 and the second count of pulses, the one or more processors may cause the acceleration structure to deliver the first count of pulses to the object according to the selected portion of the pulse sequence pattern.

In some embodiments, the one or more processors may determine a dose output rate relating to the forward window based on the DPP and the determined PRF. The one or more processors may determine whether the dose output rate is in a preset rate range. In response to a determination that the dose output rate is in the preset rate range, the one or more processors may retain the determined PRF. In response to a determination that the dose output rate is outside the preset rate range, the one or more processors may modify the determined PRF based on the DPP and the preset range rate of the forward window.

In some embodiments, the system may further include an acceleration structure configured to provide radiation pulses delivered to an object, an electron gun configured to inject electrons into the acceleration structure, a radio frequency (RF) source configured to inject electromagnetic waves into the acceleration structure to accelerate the electrons to generate the radiation pulses, and a cooling device configured to maintain at least one component in the system at an operation temperature by circulating a coolant to the at least one component. The one or more processors may obtain one or more parameters of the cooling device that are used to maintain the at least one component at the operation temperature based on a preset range. The one or more processors may cause the cooling device to operate based on the one or more parameters when the at least one component is working based on an operation parameter that is within in the preset range.

In some embodiments, the at least one component may include at least one of the acceleration structure, the electron gun, and the RF source.

According to yet another aspect of the present disclosure, a method for controlling radiation output may include one or more of the following operations. One or more processors may obtain a forward window. The forward window may be at least a portion of a treatment plan that has not been performed. The one or more processors may obtain forward information of the forward window. The forward information may include time information of the forward window, a target dose relating to the forward window, and a dose per pulse (DPP) relating to the forward window. The one or more processors may determine a pulse repetition frequency (PRF) of the forward window based on the DPP, the target dose, and the time information of the forward window. The one or more processors may obtain a pulse sequence pattern, wherein the pulse sequence pattern includes a plurality of pulse sequences during a period of time. Each of the plurality of pulse sequences may correspond to a specific PRF. Each of the plurality of pulse sequences may include a plurality of pulses and a generation time of each of the plurality of pulses. The one or more processors may select a portion of the pulse sequence pattern based on the time information of the forward window and the determined PRF of the forward window. The one or more processors may cause a radiation device to deliver one or more radiation pulses to an object according to the selected portion of the pulse sequence pattern.

According to yet another aspect of the present disclosure, a system for controlling radiation output may include a second window obtaining unit configured to obtain a forward window. The forward window may be at least a portion of a treatment plan that has not been performed. The system may also include a second information obtaining unit configured to obtain forward information of the forward window. The forward information may include time information of the forward window, a target dose relating to the forward window, and a dose per pulse (DPP) relating to the forward window. The system may also include a PRF determination unit configured to determine a pulse repetition frequency (PRF) of the forward window based on the DPP, the target dose, and the time information of the forward window. The system may also include a pattern obtaining unit configured to obtain a pulse sequence pattern, wherein the pulse sequence pattern includes a plurality of pulse sequences during a period of time. Each of the plurality of pulse sequences may correspond to a specific PRF. Each of the plurality of pulse sequences may include a plurality of pulses and a generation time of each of the plurality of pulses. The system may also include a selection unit configured to select a portion of the pulse sequence pattern based on the time information of the forward window and the determined PRF of the forward window. The system may also include a second control unit configured to cause a radiation device to deliver one or more radiation pulses to an object according to the selected portion of the pulse sequence pattern.

According to yet another aspect of the present disclosure, a non-transitory computer readable medium may comprise at least one set of instructions. The at least one set of instructions may be executed by one or more processors of a computing device. The one or more processors may obtain a forward window, the forward window being at least a portion of a treatment plan that has not been performed. The one or more processors may obtain forward information of the forward window. The forward information may include time information of the forward window, a target dose relating to the forward window, and a dose per pulse (DPP) relating to the forward window. The one or more processors may determine a pulse repetition frequency (PRF) of the forward window based on the DPP, the target dose, and the time information of the forward window. The one or more processors may obtain a pulse sequence pattern, wherein the pulse sequence pattern includes a plurality of pulse sequences during a period of time. Each of the plurality of pulse sequences may correspond to a specific PRF. Each of the plurality of pulse sequences may include a plurality of pulses and a generation time of each of the plurality of pulses. The one or more processors may select a portion of the pulse sequence pattern based on the time information of the forward window and the determined PRF of the forward window. The one or more processors may cause a radiation device to deliver one or more radiation pulses to an object according to the selected portion of the pulse sequence pattern.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "module," and/or "block" used herein are one method to distinguish different components, elements, parts, section or assembly of different level in ascending order. However, the terms may be displaced by another expression if they achieve the same purpose.

Figure 2:
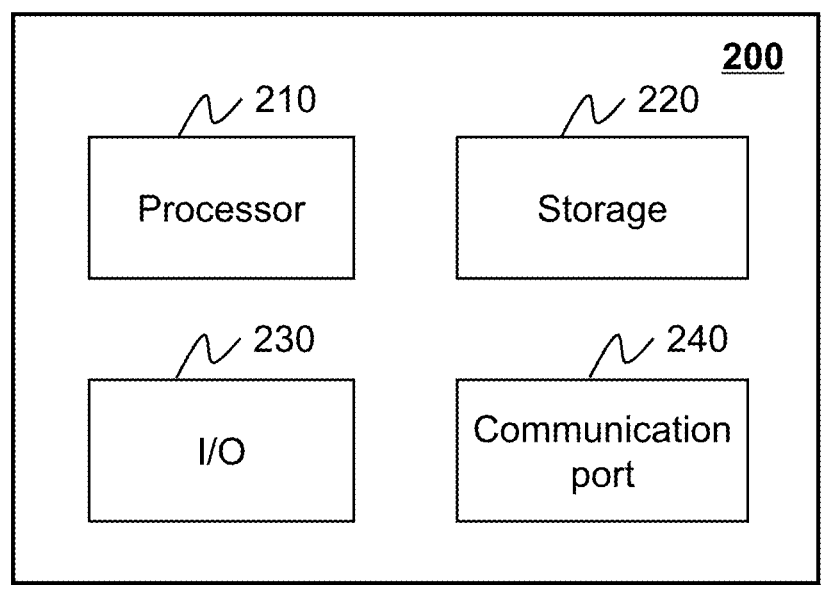
FIG. 2 is a schematic diagram illustrating hardware and/or software components of an exemplary computing device according to some embodiments of the present disclosure.

Generally, the word "module," or "block," as used herein, refers to logic embodied in hardware or firmware, or to a collection of software instructions. A module or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Electrically Programmable Read-Only-Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a module or block is referred to as being "connected to," or "coupled to," another module, or block, it may be directly connected or coupled to, or communicate with the other module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

In the present disclosure, the term "radiation output" refers to radiation output or generated in response to one or more pulses delivered by a radiation device for electron acceleration. Radiation output may be measured in Monitor Units (MU). The terms "dose" and "output" may be used interchangeably in the present disclosure.

Provided herein are systems and methods for configuring electromagnetic waves that are applied for electron acceleration in radiation generation. In an aspect of the present disclosure, a processing device may obtain a plurality of preliminary RF PRFs in a time window (e.g., a forward window within a total time of a treatment and divide the time window into a plurality of segments based on the plurality of preliminary RF PRFs. The processing device may perform a segment processing operation to determine whether a rate of variation between segment PRFs of any two neighboring (or adjacent) segments of the plurality of segments in the forward window is larger than a limit of PRF acceleration. In response to a determination that the rate of variation between the segment PRFs of two neighboring segments of the plurality of segments is larger than the limit of PRF acceleration, the processing device may process at least one of the two neighboring segments (e.g., increasing the smaller segment PRF to a certain value) to reduce the rate of variation between the two corresponding segment PRFs to less than or equal to the limit of PRF acceleration. The processing device may determine a plurality of updated RF PRFs based on the segment processing operation. By configuring the rate of variation between any two neighboring updated RF PRFs to be less than or equal to the limit of PRF acceleration, the change of two neighboring updated RF PRFs may remain relatively smooth, which may improve the stability of the RF source.

In another aspect of the present disclosure, during a treatment, the processing device may continuously modulate radiation output to make information related to delivered pulses (e.g., a radiation output rate, a cumulative radiation dose, a pulse repetition frequency (PRF), etc.) be consistent with the treatment plan. The processing device may perform the modulation based on a pulse sequence pattern. The pulse sequence pattern may include a plurality of pulse sequences during a period of time. Each of the plurality of pulse sequences may correspond to a specific PRF. Each of the plurality of pulse sequences may include a plurality of pulses and a generation time of each of the plurality of pulses. Each of the plurality of pulse sequences may further include an RF PRF and an electron PRF that facilitate the pulses delivered according to the pulse sequence. During the modulation of radiation output in the treatment, the operation of causing a radiation device to deliver pulses to an object based on the pulse sequence pattern may make the RF source output electromagnetic waves at smoothly varied RF PRFs, which improves the stability of the RF source.

Improved stability of an RF source in a radiation device may improve, e.g., the lifespan of the RF source and/or the radiation device incorporating the RF source, the consistency of the radiation output of the radiation device, and/or quality of imaging and/or efficacy and safety of radiotherapy performed based on the radiation output of the radiation device.

Figure 1A:
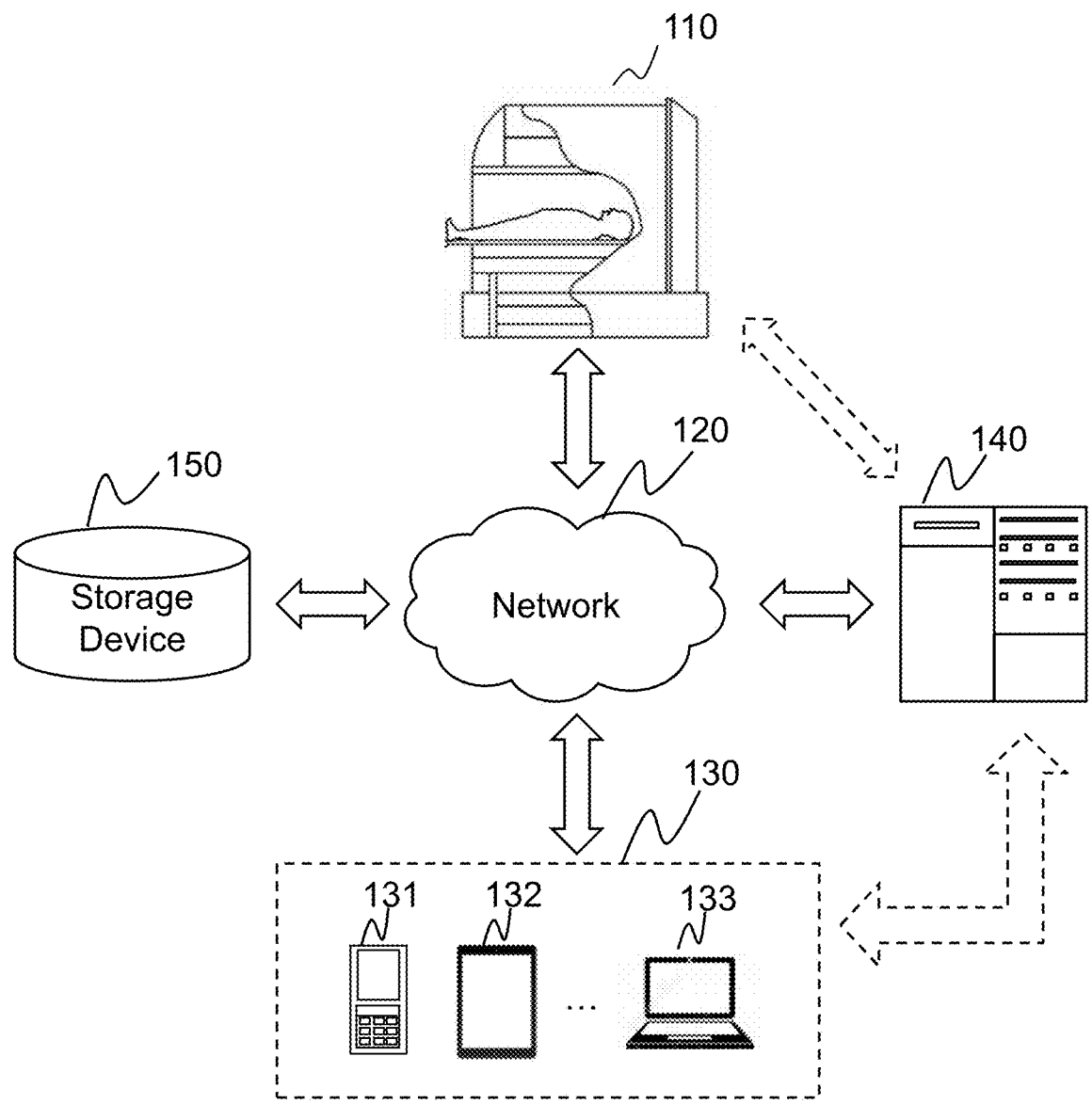
FIG. 1A is a schematic diagram illustrating an exemplary radiation output control system according to some embodiments of the present disclosure.

FIG. 1A is a schematic diagram illustrating an exemplary radiation output control system according to some embodiments of the present disclosure. As shown in FIG. 1A, the radiation output control system 100 may include a radiation device 110, a network 120, one or more terminals 130, a processing device 140, and a storage device 150.

The radiation device 110 may emit radioactive rays to a subject (e.g., a patient). The radioactive rays may include $\alpha$ rays, $\beta$ rays, $\gamma$ rays, X rays, neutrons, etc. In some embodiments, the radiation device 110 may emit radioactive rays in a form of radiation pulses. The radiation device 110 may include a medical imaging device such as an X-ray imaging device, a computed tomography (CT) device, etc., and a radiotherapy device such as an X-ray therapy device, a medical linear accelerator, a Cobalt-60 device, a Gamma knife, X knife, a proton accelerator, a brachytherapy device, etc.

In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, cardiac, stomach, blood vessel, soft tissue, knee, feet, or the like, or any combination thereof.

For brevity, the description of the methods and/or systems for controlling radiation output in this disclosure may be applied in a radiation therapy/treatment. It should be noted that the description of the methods and/or systems for controlling radiation output applied in the radiation therapy is merely provided for the purposes of illustration, and not intended to limit the scope of the present disclosure. For persons having ordinary skills in the art, multiple variations and modifications may be made under the teachings of the present disclosure. For example, the description of the methods and/or systems for controlling radiation output in this disclosure may also be applied in medical imaging (e.g., CT imaging, X-ray imaging, etc.), cargo inspection, and food sterilization. However, those variations and modifications do not depart from the scope of the present disclosure.

The radiation therapy may include a non-invasive radiation therapy, a Brachytherapy, an intraoperative radiotherapy, a radioisotope therapy, a deep inspiration breathhold (DIBH), etc. The external beam radiation therapy may include a conventional external beam radiation therapy (2DXRT), a stereotactic radiation therapy (e.g., a stereotactic radiosurgery, a stereotactic body radiation therapy, etc.), a virtual simulation and three-dimensional conformal radiation therapy (3DCRT), an intensity-modulated radiation therapy (IMRT), a volumetric modulated arc therapy (VMAT), a particle therapy, an Auger therapy (AT), etc. The radiation therapy may be used to treat a cancer or a tumor. The tumor may be in a lung, a brain, a spine, a tissue, a prostate, a breast, a cervix, an area of skin, or the like of a body.

Figure 1B:
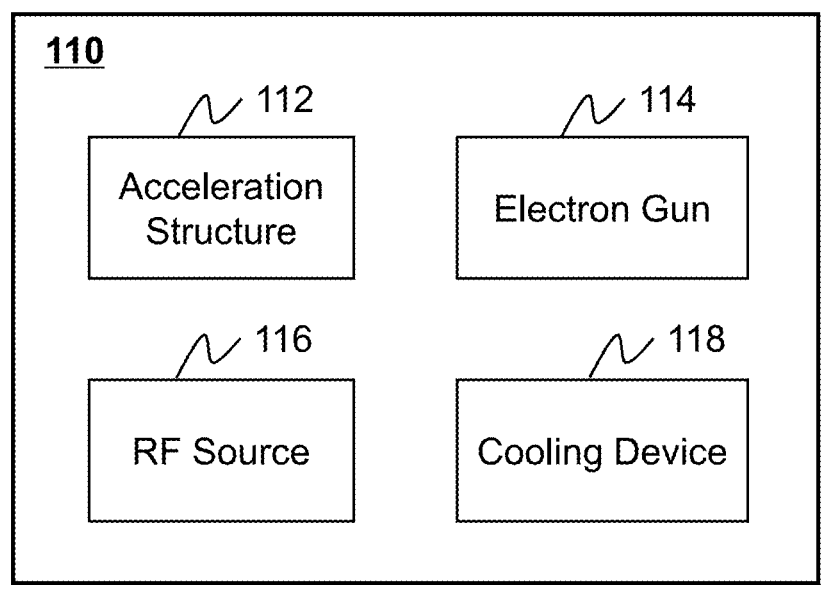
FIG. 1B is a schematic diagram illustrating an exemplary radiation device according to some embodiments of the present disclosure.

In some embodiments, as shown in FIG. 1B, the radiation device 110 may include an acceleration structure 112, an electron gun 114, and a radio frequency (RF) source 116. The acceleration structure 112 may be configured to provide radiation pulses delivered to an object at a radiation PRF. The electron gun 114 may be configured to inject electrons into the acceleration structure 112 at an electron RPF. The RF source 116 may be configured to inject electromagnetic waves (e.g., microwave pulses) into the acceleration structure 112 at an RF PRF to accelerate the electrons to generate the radiation pulses. The radiation PRF may depend on the electron PRF and the RF PRF. In some embodiments, the RF source 116 may be any suitable electromagnetic wave source such as a klystron or a magnetron.

Once the electrons have been accelerated in the acceleration structure 112, the accelerated electrons may be directed at a target, such as a tungsten or copper target, which is located at the end of the acceleration structure 112. The bombardment of the target by the accelerated electrons may generate radioactive rays.

In some embodiments, the radiation device 110 may further include a cooling device 118 configured to adjust a temperature of at least one component (e.g., the acceleration structure 112, the electron gun 114, and the RF source 116) of the radiation device 110 by circulating a coolant to the at least one component in the radiation device 110.

The network 120 may include any suitable network that can facilitate exchange of information and/or data for the radiation output control system 100. In some embodiments, one or more components of the radiation output control system 100 (e.g., the radiation device 110, the terminal 130, the processing device 140, the storage device 150, etc.) may communicate information and/or data with one or more other components of the radiation output control system 100 via the network 120. For example, the processing device 140 may obtain information related to radioactive rays from the radiation device 110 via the network 120. As another example, the processing device 140 may obtain user instructions from the terminal 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiation output control system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

The processing device 140 may process data and/or information obtained from the radiation device 110, the terminal 130, and/or the storage device 150. For example, the processing device 140 may continuously modulate radiation output to make information related to delivered pulses (e.g., a radiation output rate, a cumulative radiation dose, a pulse repetition frequency (PRF), etc.) be consistent with a treatment plan. As another example, the processing device 140 may determine RF PRFs at which the electromagnetic waves are output by the RF source 116 to improve the stability of the RF source 116. In some embodiments, the processing device 140 may be a single server or a server group. The server group may be centralized or distributed. In some embodiments, the processing device 140 may be local or remote. For example, the processing device 140 may access information and/or data stored in the radiation device 110, the terminal 130, and/or the storage device 150 via the network 120. As another example, the processing device 140 may be directly connected to the radiation device 110, the terminal 130 and/or the storage device 150. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the radiation device 110, the terminal 130, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiation output control system 100 (e.g., the radiation device 110, the processing device 140, the terminal 130, etc.). One or more components in the radiation output control system 100 may access the data or instructions stored in the storage device 150 via the network 120. In some embodiments, the storage device 150 may be directly connected to or communicate with one or more other components in the radiation output control system 100 (e.g., the radiation device 110, the processing device 140, the terminal 130, etc.). In some embodiments, the storage device 150 may be part of the processing device 140.

FIG. 2 is a schematic diagram illustrating hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may continuously modulate radiation output so that the delivered pulses (e.g., a radiation output rate, a cumulative radiation dose, a pulse repetition frequency (PRF) related to the radiation output, etc.) are consistent with a treatment plan. As another example, the processor 210 may determine RF PRFs at which the electromagnetic waves are output by the RF source 116 to improve the stability of the RF source 116. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both step X and step Y, it should be understood that step X and step Y may also be performed by two or more different processors jointly or separately in the computing device 200 (e.g., a first processor executes step X and a second processor executes step Y, or the first and second processors jointly execute steps X and Y).

The storage 220 may store data/information obtained from the radiation device 110, the terminal 130, the storage device 150, and/or any other component of the radiation output control system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. Exemplary removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for controlling radiation output.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiation device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with digital imaging and communications in medicine (DI-COM) protocol.

Figure 3:
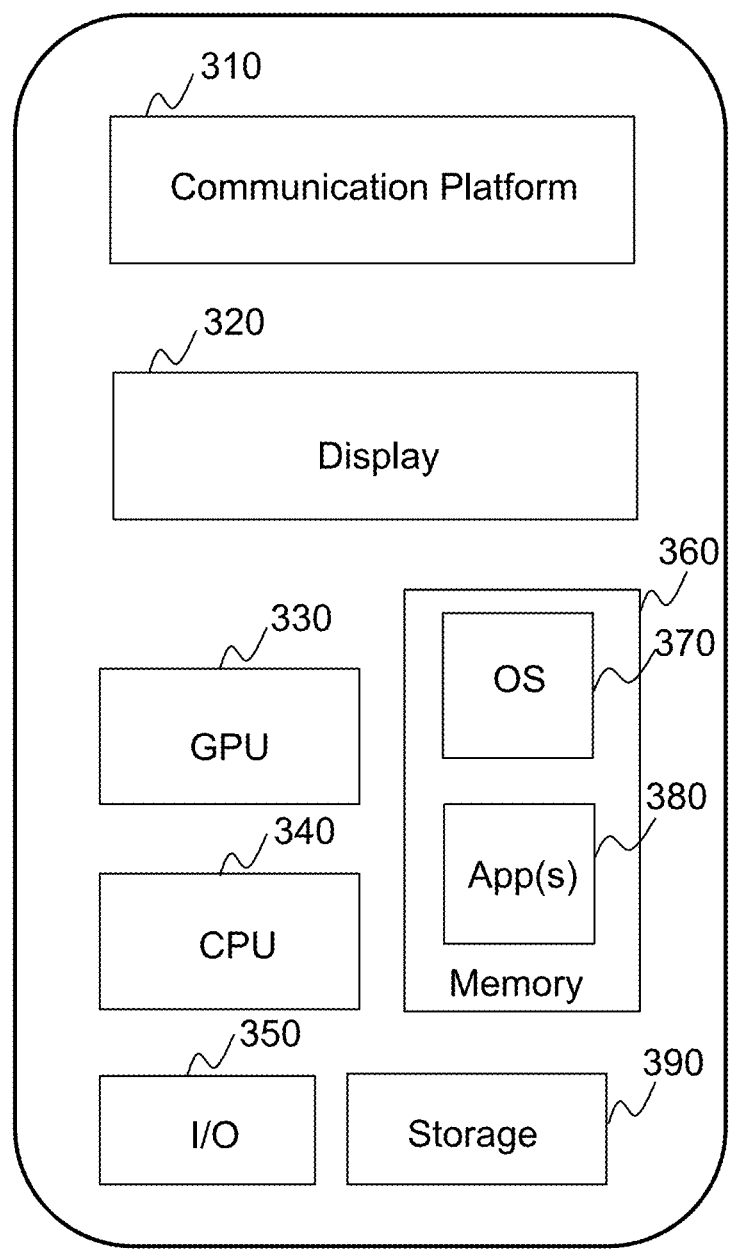
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation output control system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
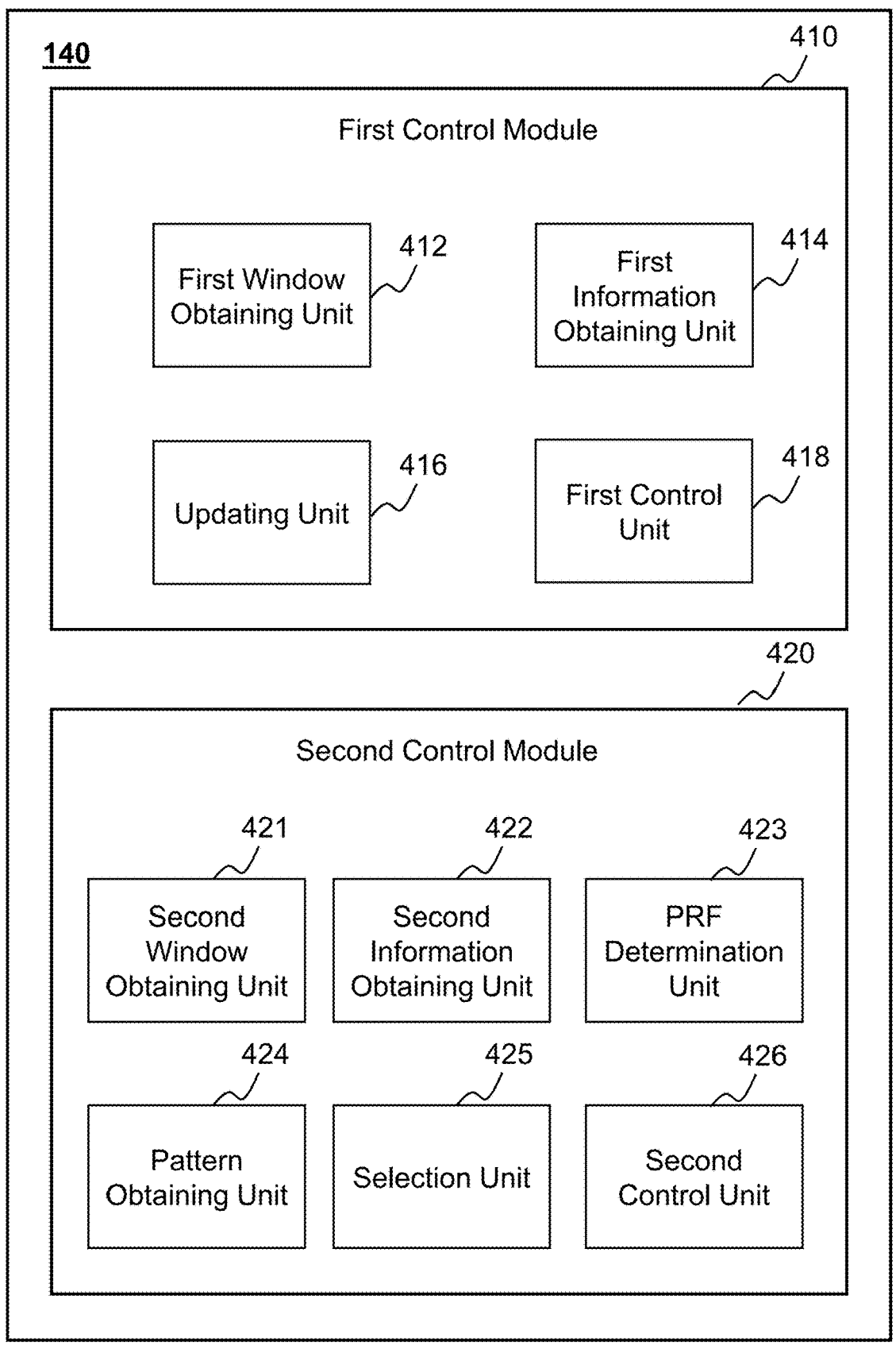
FIG. 4 is a block diagram illustrating an exemplary processing device according to some embodiments of the present disclosure.

FIG. 4 is a block diagram illustrating an exemplary processing device according to some embodiments of the present disclosure. In some embodiments, the processing device 140 may include a first control module 410 and a second control module 420. The first control module 410 may be configured to perform operations for determining RF PRFs at which the electromagnetic waves are output by the RF source 116 to improve the stability of the RF source 116. The second control module 420 may be configured to continuously modulate radiation output so that the delivered pulses (e.g., a radiation output rate, a cumulative radiation dose, a pulse repetition frequency (PRF) related to the radiation output, etc.) are consistent with a treatment plan.

In some embodiments, the first control module 410 may include a first window obtaining unit 412, a first information obtaining unit 414, an updating unit 416, and a first control unit 418.

The first window obtaining unit 412 may identify a time window. For instance, the time window may be a forward window corresponding to at least a portion of a treatment plan that has not been performed.

In some embodiments, the first window obtaining unit 412 may determine the time window automatically. For example, the first window obtaining unit 412 may determine the current time (e.g., a time when the radiation device 110 finishes delivering a radiation pulse and now is about to deliver another radiation pulse) as a start time of a time window and a time point after the current time as an end time of the time window automatically. The first window obtaining unit 412 may determine the time window based on the start time and the end time. In some embodiments, the first window obtaining unit 412 may determine the time window based on instructions from a user (e.g., a doctor). For example, the user may input a start time (e.g., the current time) and an end time after the current time through the processing device 140 (e.g., the I/O 230) and/or the terminal 130 (e.g., the I/O 350) and send instructions related to the start time and the end time to the first window obtaining unit 412. After receiving the instructions, the first window obtaining unit 412 may determine the time window based on the start time and the end time.

The first information obtaining unit 414 may obtain operational information of the time window. In some embodiments, the first information obtaining unit 414 may obtain the information related to the treatment plan and obtain the operational information based on the information related to the treatment plan.

In some embodiments, the operational information may include a forward start time of the time window, a forward end time of the time window, a forward interval of the time window, a limit of PRF acceleration, a plurality of preliminary RF PRFs corresponding to the time window, or the like, or any combination thereof. When the output of electromagnetic waves switches between two different RF PRFs, the RF source 116 may perform a transition operation to realize the switch. The limit of PRF acceleration may refer to a maximum rate of variation between two different RF PRFs in the transition operation. In some embodiments, the operational information may further include a minimum duration of an RF PRF. The minimum duration of an RF PRF may refer to a minimum duration for which the RF source continuously outputs electromagnetic waves at a same RF PRF.

In some embodiments, the forward start time or the forward end time of a time window may coincide with one of the plurality of control points, or the forward start time and the forward end time of a time window may coincide with two of the plurality of control points, respectively. In some embodiments, the forward start time and the forward end time do not coincide with any of the plurality of control points.

The updating unit 416 may determine a plurality of updated RF PRFs by updating the plurality of preliminary RF PRFs. A rate of variation between any two neighboring updated RF PRFs may be less than or equal to the limit of PRF acceleration, so that the change of two neighboring updated RF PRFs is relatively smooth, which may improve the stability of the RF source 116.

The first control unit 418 may cause the RF source 116 to output electromagnetic waves. In some embodiments, when the treatment proceeds to the portion corresponding to the time window, the first control unit 418 may cause the RF source 116 to output electromagnetic waves based on the updated RF PRFs corresponding to the time window.

In some embodiments, the second control module 420 may include a second window obtaining unit 421, a second information obtaining unit 422, a PRF determination unit 423, a pattern obtaining unit 424, a selection unit 425, and a second control unit 426.

The second window obtaining unit 421 may obtain a forward window. The forward window may be at least a portion of a treatment plan that has not been performed.

In some embodiments, the forward window may refer to a time window after the current treatment stage. In some embodiments, the second window obtaining unit 421 may determine the forward window automatically. For example, the second window obtaining unit 421 may determine the current time as a start time of a forward window and a time point after the current time as the end time of the forward window automatically. The second window obtaining unit 421 may determine the forward window based on the start time and the end time. In some embodiments, the second window obtaining unit 421 may determine the forward window based on instructions from a user (e.g., a doctor). For example, the user may input a start time (e.g., the current time) and an end time after the current time through the processing device 140 (e.g., the I/O 230) and/or the terminal 130 (e.g., the I/O 350) and send instructions related to the start time and the end time to the second window obtaining unit 421. After receiving the instructions, the second window obtaining unit 421 may determine the forward window based on the start time and the end time.

The second information obtaining unit 422 may obtain forward information of the forward window. In some embodiments, the second information obtaining unit 422 may obtain the information related to the treatment plan and obtain the forward information based on the information related to the treatment plan.

The forward information may include time information (e.g., a forward start time of the forward window, a forward end time of the forward window, a forward interval of the forward window, etc.), a forward cumulative radiation dose (also referred to as a target dose) of the forward window, a dose per pulse (DPP) related to the forward window, or the like, or any combination thereof. The forward cumulative radiation dose may refer to a radiation dose delivered in response to a plurality of pulses from the start time of the treatment to the forward end time. In some embodiments, the forward start time or the forward end time may coincide with one of the plurality of control points, or the forward start time and the forward end time may coincide with two of the plurality of control points, respectively, or the forward start time and the forward end time may not coincide with any of the plurality of control points.

The DPP related to the forward window may refer to the DPP in response to one or more pulses that have been delivered during a backward period within the total time of the treatment before the forward window. In some embodiments, when the radiation device 110 delivers pluses during the treatment, the radiation device 110, the processing device 140 or the terminal 130 may record the delivery times at which the pulses are delivered, the cumulative radiation dose that has been delivered, and the number (or count) of pulses that have been delivered, etc. In some embodiments, the second information obtaining unit 422 may select a backward period as close as possible to the forward window. For example, the end time of the backward period and the start time of the forward window may be the same. The second information obtaining unit 422 may obtain the actual recorded radiation output and the actual recorded number of pulses in response to one or more pulses that have been delivered during the backward period. The second information obtaining unit 422 may determine the DPP by dividing the actual recorded radiation output by the actual recorded number of pulses.

The second information obtaining unit 422 may determine the forward cumulative radiation dose based on the information related to the treatment plan. In some embodiments, there may be a relationship between a time point within the total time of the treatment and a cumulative radiation dose associated with the time point (e.g., indicating a radiation dose from the start time of the treatment to the time point). In some embodiments, the second information obtaining unit 422 may determine the relationship based on the cumulative radiation doses associated with the control time points related to the treatment plan. In some embodiments, the second information obtaining unit 422 may determine the relationship by fitting a continuity equation or a discrete equation. In some embodiments, the fitting method may include interpolation, extrapolation, smoothing, regression analysis, the least square method, or the like, or any combination thereof. Exemplary interpolation algorithms may include Lagrange interpolation, Newton interpolation, Hermite interpolation, piecewise interpolation, spline interpolation, linear interpolation, or the like, or a combination thereof. Exemplary extrapolation algorithms may include linear extrapolation, polynomial extrapolation, conic extrapolation, French curve extrapolation, linear predictors, Kalman filtering, extended Kalman filtering, neural-network predictors, or the like, or a combination thereof. Exemplary techniques for a regression analysis may include linear regression, nonlinear regression, multiple regression, logistic regression, partial regression, or the like, or a combination thereof. With the determined relationship (e.g., a planned cumulative radiation function), the second information obtaining unit 422 may determine a cumulative radiation dose associated with any time point within the total time of the treatment. For example, if the forward end time coincides with a control point, the second information obtaining unit 422 may determine the forward cumulative radiation dose based on the cumulative radiation dose associated with the control point in the treatment plan. As another example, if the forward end time does not coincide with any control points, the second information obtaining unit 422 may determine the forward cumulative radiation dose based on the planned cumulative radiation function.

The PRF determination unit 423 may determine a pulse repetition frequency (PRF) of the forward window based on the DPP, the target dose, and the time information of the forward window.

A forward radiation dose may refer to a radiation dose delivered in response to one or more pulses during the forward interval of the forward window. The PRF determination unit 423 may determine the forward radiation dose based on the forward cumulative radiation dose. In some embodiments, the PRF determination unit 423 may determine the forward radiation dose by subtracting a cumulative radiation dose associated with the forward start time (e.g., the current time) from a cumulative radiation dose associated with the forward end time (e.g., the forward cumulative radiation dose). In a condition that the forward start time is equal to the current time, the PRF determination unit 423 may determine the cumulative radiation dose of the current time (e.g., an actually recorded radiation dose delivered in response to one or more pulses that have been transmitted during a time period from the start time of the treatment to the current time) as the cumulative radiation dose associated with the forward start time. In a condition that the forward start time is later than the current time (e.g., a time when the radiation device 110 finishes delivering a radiation pulse and now is about to deliver another radiation pulse), the PRF determination unit 423 may determine the cumulative radiation dose associated with the forward start time based on the planned cumulative radiation function.

In some embodiments, the PRF determination unit 423 may determine the number of pulses delivered during the forward interval by dividing the forward radiation dose by the DPP. The PRF determination unit 423 may determine the PRF of the forward window by dividing the number of pulses delivered during the forward interval by the forward interval.

The pattern obtaining unit 424 may obtain a pulse sequence pattern. The pulse sequence pattern may include a plurality of pulse sequences during a period of time. Each of the plurality of pulse sequences may correspond to a specific PRF. Each of the plurality of pulse sequences may include a plurality of pulses and a generation time of each of the plurality of pulses. In some embodiments, each of the plurality of pulse sequences may further include an RF PRF and an electron PRF that facilitate the pulses delivered according to the pulse sequence.

The selection unit 425 may select a portion of the pulse sequence pattern based on the time information of the forward window and the determined PRF of the forward window. For example, the total time of the treatment is 35 seconds. The forward interval of the forward window is 40-80 ms within the total time. The PRF of the forward window determined in operation 1030 is 150 Hz. The selection unit 425 may select a portion of the pulse sequence pattern 1001 in FIG. 10B corresponding to 150 Hz and a time period of 40-80 ms.

The second control unit 426 may cause the radiation device 110 to deliver one or more radiation pulses to an object according to the selected portion of the pulse sequence pattern.

In some embodiments, the second control unit 426 may cause the electron gun 114 to inject electrons into the acceleration structure 112 at an electron frequency corresponding to the selected portion of the pulse sequence pattern. The second control unit 426 may cause the RF source 116 to inject electromagnetic waves into the acceleration structure 112 at an RF PRF corresponding to the selected portion of the pulse sequence pattern. The second control unit 426 may cause the acceleration structure 112 to deliver, based on the injected electrons and the electromagnetic waves, the one or more radiation pulses to the object.

In some embodiments, the first control module 410 or the second control module 420 may be omitted.

The modules in the processing device 140 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules/units may be combined as a single module/unit, and any one of the modules/units may be divided into two or more blocks. For example, the pattern obtaining unit 424 and the selection unit 425 may be integrated as a single unit which may both obtaining a pulse sequence pattern and select a portion of the pulse sequence pattern.

It should be noted that the above description of the processing device 140 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of the components of the processing device 140 may include a storage device. Additionally or alternatively, the components of the processing device 140 may share a common storage device.

In some embodiments, before a treatment is performed to a patient, a treatment plan of the treatment may be made based on, for example, a condition of and/or a desired treatment outcome for the patient. Information related to the treatment plan may include a total time of the treatment, a plurality of control time points within the total time of the treatment, a total radiation dose during the total time of the treatment, a cumulative radiation dose associated with each of the plurality of control time points, an duration of a treatment session of the treatment between each two neighboring control time points within the total time of the treatment, a radiation output rate during each treatment session, a radiation PRF during each treatment session, a preliminary RF PRF during each treatment session, or the like, or any combination thereof. The cumulative radiation dose associated with a control point may refer to a radiation dose delivered in a plurality of pulses from the start of the treatment to a control point of the treatment.

In some embodiments, a user of the system 100 (e.g., a doctor) may set the information related to the treatment plan before the treatment commences. In some embodiments, the user may set the information related to the treatment plan through a user interface communicating with the processing device 140 (e.g., the I/O 230) and/or implemented on the terminal 130 (e.g., the I/O 350). In some embodiments, the information related to the treatment plan may be stored in a storage medium (e.g., the storage device 150, the storage 220 of the processing device 140, the storage 390 of the terminal 130, the memory 360 of the terminal 130, etc.) of the radiation output control system 100. The processing device 140 may obtain the information related to the treatment plan by accessing the storage medium.

In some embodiments, for a same treatment session, the preliminary RF PRF may be similar to the radiation PRF. There may be a case in which a difference between two neighboring preliminary RF PRFs is relatively large so that there may be an abrupt output change when the RF source 116 outputs electromagnetic waves at the two neighboring preliminary RF PRFs, which may reduce the stability of the RF source 116. Embodiments of the present disclosure provides systems and/or methods for updating the preliminary RF PRFs so that the change of any two neighboring updated RF PRFs may be relatively smooth. The description in connection with FIGS. 5-9 illustrates some embodiments of the systems and/or methods for updating the preliminary RF PRFs provided in the present disclosure.

Figure 5:
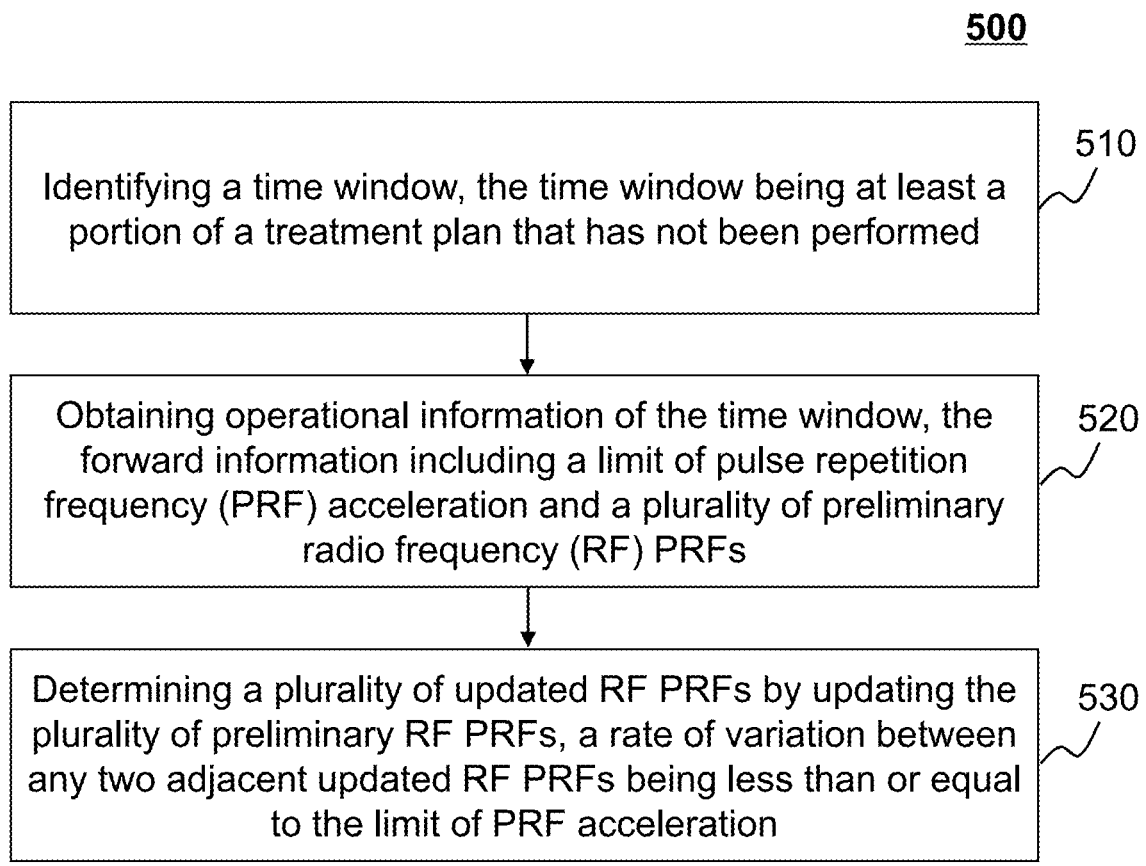
FIG. 5 is a flowchart illustrating an exemplary process for determining a plurality of updated RF PRFs according to some embodiments of the present disclosure.

FIG. 5 is a flowchart illustrating an exemplary process for determining a plurality of updated RF PRFs according to some embodiments of the present disclosure. In some embodiments, the process 500 may be implemented in the system 100 illustrated in FIG. 1. For example, the process 500 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process presented below are intended to be illustrative. In some embodiments, the process 500 may be accomplished with one or more additional operations not described, and/or without one or more of the operations discussed. Additionally, the order in which the operations of the process as illustrated in FIG. 5 and described below is not intended to be limiting.

In 510, the processing device 140 (e.g., the first control module 410 or the first window obtaining unit 412) may identify a time window. For instance, the time window may be a forward window corresponding to at least a portion of a treatment plan that has not been performed.

In some embodiments, the processing device 140 may perform the process 500 to process all of the preliminary RF PRFs in the treatment plan at once before a treatment corresponding to the treatment plan is performed to a patient. In this case, the forward window may correspond to the entire treatment plan. In some embodiments, the processing device may perform the process 500 to process the preliminary RF PRFs after a portion of a treatment has been performed. In this case, the forward window may correspond to the portion of the treatment (including one or more treatment sessions) that has not been performed. As used herein, a treatment may be used to refer an entire treatment including one or more treatment sessions or a portion of a treatment including, e.g., one or more treatment sessions.

In some embodiments, the processing device 140 may perform the process 500 to process a part of the preliminary RF PRFs in the treatment plan during the treatment. In this case, the time window may be a forward window corresponding to the portion of the treatment that has not been performed.

In some embodiments, the processing device 140 may determine the time window automatically. For example, the processing device 140 may determine the current time (e.g., a time when the radiation device 110 finishes delivering a radiation pulse and now is about to deliver another radiation pulse) as a start time of a time window and a time point after the current time as an end time of the time window automatically. The processing device 140 may determine the time window based on the start time and the end time. In some embodiments, the processing device 140 may determine the time window based on instructions from a user (e.g., a doctor). For example, the user may input a start time (e.g., the current time) and an end time after the current time through the processing device 140 (e.g., the I/O 230) and/or the terminal 130 (e.g., the I/O 350) and send instructions related to the start time and the end time to the processing device 140. After receiving the instructions, the processing device 140 may determine the time window based on the start time and the end time.

In some embodiments, during the treatment, the processing device 140 may determine a plurality of time windows and process the preliminary RF PRFs in each time window by repeating the process 500. The intervals of the plurality of time windows may be the same (e.g., 1 second, 2 seconds, 3 seconds, etc.) or different.

In 520, the processing device 140 (e.g., the first control module 410 or the first information obtaining unit 414) may obtain operational information of the time window. In some embodiments, the processing device 140 may obtain the information related to the treatment plan and obtain the operational information based on the information related to the treatment plan.

In some embodiments, the operational information may include a forward start time of the time window, a forward end time of the time window, a forward interval of the time window, a limit of PRF acceleration, a plurality of preliminary RF PRFs corresponding to the time window, or the like, or any combination thereof. When the output of electromagnetic waves switches between two different RF PRFs, the RF source 116 may perform a transition operation to realize the switch. The limit of PRF acceleration may refer to a maximum rate of variation between two different RF PRFs in the transition operation. In some embodiments, the operational information may further include a minimum duration of an RF PRF. The minimum duration of an RF PRF may refer to a minimum duration for which the RF source continuously outputs electromagnetic waves at a same RF PRF.

In some embodiments, the forward start time or the forward end time of a time window may coincide with one of the plurality of control points, or the forward start time and the forward end time of a time window may coincide with two of the plurality of control points, respectively. In some embodiments, the forward start time and the forward end time do not coincide with any of the plurality of control points.

In 530, the processing device 140 (e.g., the first control module 410 or the updating unit 416) may determine a plurality of updated RF PRFs by updating the plurality of preliminary RF PRFs. A rate of variation between any two neighboring updated RF PRFs may be less than or equal to the limit of PRF acceleration, so that the change of two neighboring updated RF PRFs is relatively smooth, which may improve the stability of the RF source 116. In some embodiments, when the treatment proceeds to the portion corresponding to the time window, the processing device 140 may cause the RF source 116 to output electromagnetic waves based on the updated RF PRFs corresponding to the time window.

Details regarding the determination of the updated RF PRFs may be found elsewhere in the present disclosure (e.g., the description in connection with FIGS. 6-9). For simplicity and illustration purposes, the descriptions of FIGS. 6-9, as well as the descriptions of FIG. 4 and FIGS. 10A-14 refer to a forward window as the time window described in connection with FIG. 5. It is understand that this is not intended to be limiting.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 6:
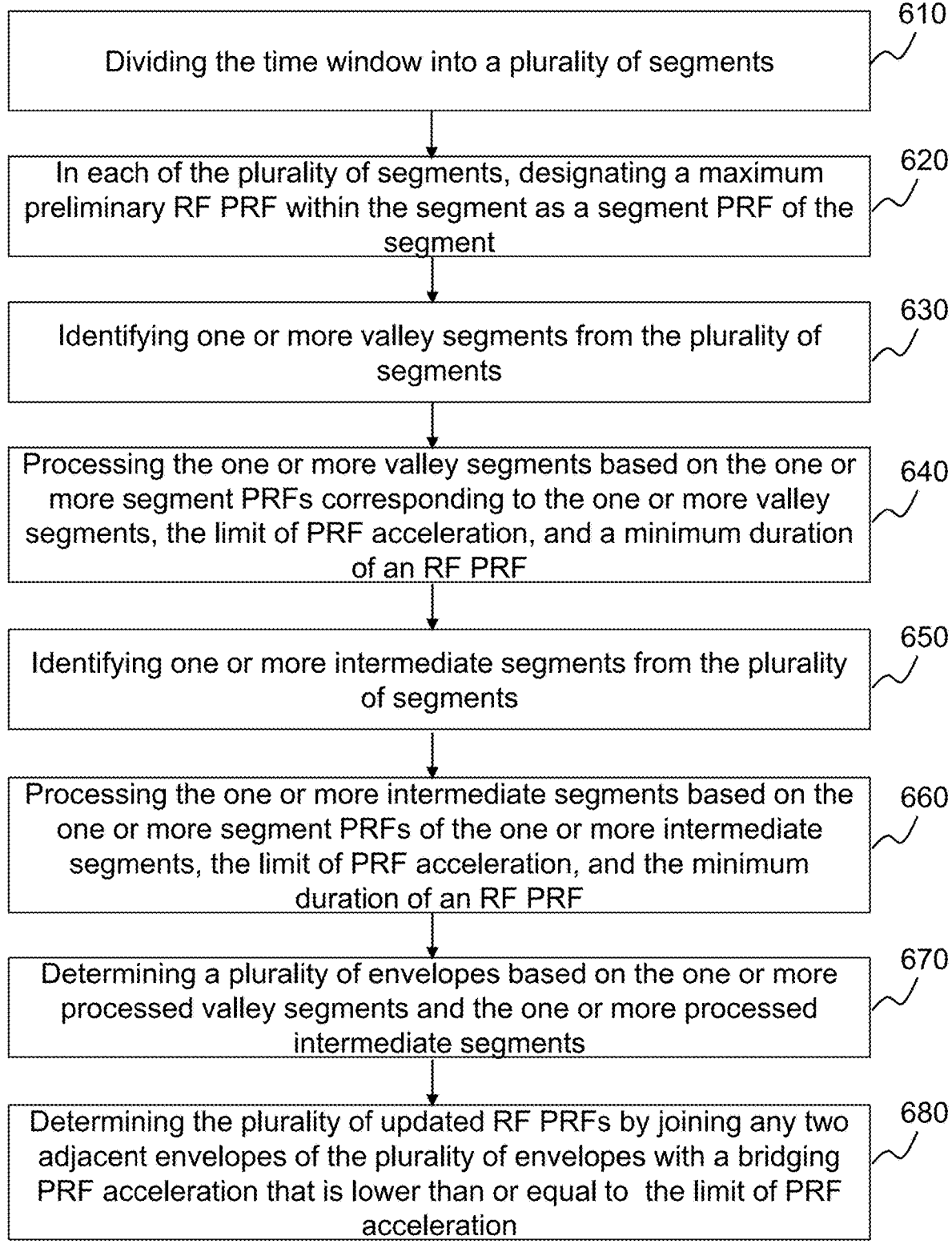
FIG. 6 is a flowchart illustrating an exemplary process for determining a plurality of updated RF PRFs according to some embodiments of the present disclosure.

FIG. 6 is a flowchart illustrating an exemplary process for determining a plurality of updated RF PRFs according to some embodiments of the present disclosure. In some embodiments, the process 600 may be implemented in the system 100 illustrated in FIG. 1. For example, the process 600 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 600 presented below are intended to be illustrative. In some embodiments, the process 600 may be accomplished with one or more additional operations not described, and/or without one or more of the operations discussed. Additionally, the order in which the operations of the process as illustrated in FIG. 6 and described below is not intended to be limiting. In some embodiments, the processing device 140 may perform operation 530 in the process 500 in FIG. 5 based on the process 600.

In 610, the processing device 140 (e.g., the first control module 410 or the updating unit 416) may divide the forward window into a plurality of segments. In some embodiments, the segment may include one preliminary RF PRF, or two or more consecutive preliminary RF PRFs. For example, the processing device 140 may determine one of the treatment sessions in the forward window plan as a segment. As another example, the processing device 140 may combine two or more consecutive treatment sessions in the forward window as a segment. A difference between any two of the preliminary RF PRFs of the two or more consecutive treatment sessions in the segment may be less than a difference threshold.

In 620, the processing device 140 (e.g., the first control module 410 or the updating unit 416) may designate, in each of the plurality of segments, a maximum preliminary RF PRF within the segment as a segment PRF of the segment. In some embodiments, if two or more consecutive segments have a same segment PRF, the processing device 140 may merge the two or more consecutive segments as a single segment.

In some embodiments, the processing device 140 may perform a segment processing operation that may be an iteration process including one or more iterations to determine whether the rate of variation between the segment PRFs of any two neighboring segments of the plurality of segments in the forward window is larger than the limit of PRF acceleration. In response to a determination that the rate of variation between the segment PRFs of two neighboring segments of the plurality of segments is larger than the limit of PRF acceleration, the processing device 140 may process at least one of the two neighboring segments to make the rate of variation between the two corresponding segment PRFs less than or equal to the limit of PRF acceleration. In response to a determination that the rate of variation between the segment PRFs of two neighboring segments of the plurality of segments is less than or equal to the limit of PRF acceleration, the processing device 140 may retain the two neighboring segments.

In some embodiments, each of the one or more iterations may include operations 630-660.

In 630, the processing device 140 (e.g., the first control module 410 or the updating unit 416) may identify one or more valley segments from the plurality of segments in the forward window. In some embodiments, the segment PRF of the valley segment may be less than the segment PRFs of valley adjacent segments of the valley segment. The valley adjacent segments and the valley segment may be three consecutive segments in the forward window with the valley segment in the middle.

In 640, the processing device 140 (e.g., the first control module 410 or the updating unit 416) may process the one or more valley segments based on the one or more segment PRFs corresponding to the one or more valley segments, the limit of PRF acceleration, and the minimum duration of an RF PRF.

In some embodiments, for each of the one or more valley segments, the processing device 140 may determine a first sum of a de-acceleration time of the valley segment, an acceleration time of the valley segment, and the minimum duration of an RF PRF. For example, in the valley adjacent segments, the processing device 140 may determine a first difference between the segment PRF of the segment prior to the valley segment and the segment PRF of the valley segment. The processing device 140 may determine the de-acceleration time based on the first difference and the limit of PRF acceleration, e.g., by dividing the first difference by the limit of PRF acceleration. The processing device 140 may determine a second difference between the segment PRF of the segment immediately following the valley segment and the segment PRF of the valley segment. The processing device 140 may determine the acceleration time based on the second difference and the limit of PRF acceleration, e.g., by dividing the second difference by the limit of PRF acceleration.

The processing device 140 may determine whether the first sum is shorter than or equal to a segment time (e.g., a duration) of the valley segment. In response to a determination that the first sum is shorter than or equal to the segment time of the valley segment, the processing device 140 may retain the valley segment. In response to a determination that the first sum is longer than the segment time of the valley segment, the processing device 140 may merge the valley segment with a first adjacent segment of the valley adjacent segments by increasing the segment PRF of the valley segment to the segment PRF of the first adjacent segment. The segment PRF of the first adjacent segment may be less than the segment PRF of a second adjacent segment of the valley adjacent segments.

In some embodiments, according to operation 630, the processing device 140 may examine the segments in the forward window in any order (e.g., from a start to an end or from the end to the start of the forward window) to identify the one or more valley segments. Then, according to operation 640, the processing device 140 may process the one or more identified valley segments in any order. For example, the processing device 140 may process the one or more identified valley segments from the start to the end or from the end to the start of the forward window. As another example, the processing device 140 may simultaneously process at least a portion of the one or more identified valley segments.

In some embodiments, the processing device 140 may examine each of the plurality of segments from the start to the end or from the end to the start of the forward window based on operations 630-640. For example, because the first segment of the forward window is impossible to be the valley segment, the processing device 140 may perform the examination starting from the second segment. The processing device 140 may determine whether the second segment of the forward window is the valley segment. In response to a determination that the second segment is the valley segment, the processing device 140 may process the second segment based on operation 640. Then the processing device 140 may examine the third segment (e.g., immediately following the second segment) based on the processed second segment. In response to a determination that the second segment is not the valley segment, the processing device 140 may proceed to examine the third segment (e.g., immediately following the second segment) of the forward window. The rest segments may be processed in the same manner until the last segment in the forward window.

In 650, the processing device 140 (e.g., the first control module 410 or the updating unit 416) may identify one or more intermediate segments from the plurality of segments in the forward window. The segment PRF of the intermediate segment may be less than the segment PRF of only one of one or more intermediate adjacent segments of the intermediate segment. The one or more intermediate adjacent segments and the intermediate segment may be three consecutive segments in the forward window with the intermediate segment in the middle or two consecutive segments (e.g., the intermediate segment is the first or last segment in the forward window) in the forward window.

In 660, the processing device 140 (e.g., the first control module 410 or the updating unit 416) may process the one or more intermediate segments based on the one or more segment PRFs of the one or more intermediate segments, the limit of PRF acceleration, and the minimum duration of an RF PRF.

In some embodiments, for each of the one or more intermediate segments, the processing device 140 may determine a second sum of a de-acceleration time or an acceleration time of the intermediate segment plus the minimum duration of an RF PRF. For example, the processing device 140 may determine a third difference between the segment PRF of a third adjacent segment and the segment PRF of the intermediate segment. The third adjacent segment may be one of the one or more intermediate adjacent segments and the segment PRF of the third adjacent segment may be larger than the segment PRF of the intermediate segment. The processing device 140 may determine the de-acceleration time or the acceleration time based on the third difference and the limit of PRF acceleration, e.g., by dividing the third difference by the limit of PRF acceleration. For example, if the third adjacent segment is prior to the intermediate segment, the result of dividing the third difference by the limit of PRF acceleration may be referred to as the de-acceleration time. If the third adjacent segment is immediately following the intermediate segment, the result of dividing the third difference by the limit of PRF acceleration may be referred to as the acceleration time.

The processing device 140 may determine whether the second sum is shorter than or equal to a segment time (e.g., a duration) of the intermediate segment. In response to a determination that the second sum is shorter than or equal to the segment time of the intermediate segment, the processing device 140 may retain the intermediate segment. In response to a determination that the second sum is longer than the segment time of the intermediate segment, the processing device 140 may merge the intermediate segment with the third adjacent segment of the one or more intermediate adjacent segments by increasing the segment PRF of the intermediate segment to the segment PRF of the third adjacent segment.

In some embodiments, according to operation 650, the processing device 140 may examine the segments in the forward window in any order (e.g., from the start to the end or from the end to the start of the forward window) to identify the one or more intermediate segments. Then, according to operation 660, the processing device 140 may process the one or more identified intermediate segments in any order. For example, the processing device 140 may process the one or more identified intermediate segments from a start to an end or from the end to the start of the forward window. As another example, the processing device 140 may simultaneously process at least a portion of the one or more identified intermediate segments.

In some embodiments, the processing device 140 may examine each of the plurality of segments from the start to the end or from the end to the start of the forward window based on operations 650-660. For example, the processing device 140 may determine whether the first segment of the forward window is the intermediate segment. In response to a determination that the first segment is the intermediate segment, the processing device 140 may process the first segment based on operation 660. Then the processing device 140 may examine the second segment (e.g., immediately following the first segment) based on the processed first segment. In response to a determination that the first segment is not the intermediate segment, the processing device 140 may proceed to examine the second segment (e.g., immediately following the first segment) of the forward window. The rest segments may be processed in the same manner until the last segment in the forward window.

In some embodiments, the processing device 140 may perform the operations (e.g., operations 630-640) for identifying and processing the one or more valley segments before or after the operations (e.g., operations 650-660) for identifying and processing the one or more intermediate segments. For example, if the processing device 140 performs the operations for identifying and processing the one or more valley segments before the operations for identifying and processing the one or more intermediate segments, the processing device 140 may identify and process the one or more intermediate segments from the plurality of segments based on the one or more processed valley segments (e.g., from the plurality of segments including the one or more processed valley segments). As another example, if the processing device 140 performs the operations for identifying and processing the one or more valley segments after the operations for identifying and processing the one or more intermediate segments, the processing device 140 may identify the one or more valley segments from the plurality of segments based on the one or more processed intermediate segments (e.g., from the plurality of segments including the one or more processed intermediate segments).

In some embodiments, the processing device 140 may examine each of the plurality of segments from the start to the end or from the end to the start of the forward window based on operations 630-660. For example, the processing device 140 may determine whether the first segment at the start of the forward window is the intermediate segment. In response to a determination that the first segment is the intermediate segment, the processing device 140 may process the first segment based on operation 660. Then the processing device 140 may determine whether the second segment (e.g., immediately following the first segment) of the forward window is the valley segment or the intermediate segment based on the processed first segment. In response to a determination that the second segment is the valley segment or the intermediate segment, the processing device 140 may process the second segment based on operation 640 or operation 660. The rest segments may be processed in the same manner until the last segment in the forward window.

In some embodiments, segment merging may lead to one or more new valley segments and/or one or more new intermediate segments. The new valley segment or the new intermediate segment may refer to a valley segment or an intermediate segment of which the segment PRF has not been compared with the segment PRFs of the segments adjacent to the valley segment or the intermediate segment. For example, the segment merging may lead to a merged segment that is also a valley segment or an intermediate segment. The merged segment may be determined as a new valley segment or a new intermediate segment. As another example, the segment merging may change at least one of a retained valley segment's adjacent segments or a retained intermediate segment's adjacent segments, which may make the retained valley segment or the retained intermediate segment become a new valley segment or a new intermediate segment.

After one of the one or more iterations (e.g., operations 630-660), the processing device 140 may initiate a new iteration (e.g., repeat operations 630-660) to identify and process one or more new valley segments and/or one or more new intermediate segments, until no new valley segment and no new intermediate segment is formed, e.g., all of the valley segments and the intermediate segments are retained in the current iteration.

In 670, the processing device 140 (e.g., the first control module 410 or the updating unit 416) may determine a plurality of envelopes based on the one or more processed valley segments and the one or more processed intermediate segments. In some embodiments, each of the plurality of envelopes may correspond to a retained segment in the forward window after the iteration process described above.

In 680, the processing device 140 (e.g., the first control module 410 or the updating unit 416) may determine the plurality of updated RF PRFs by joining any two adjacent envelopes of the plurality of envelopes with a bridging PRF acceleration that is lower than or equal to the limit of PRF acceleration. The bridging PRF acceleration may refer to a rate of variation between two different RF PRFs in the transition operation. In some embodiments, each of the plurality of updated RF PRFs may correspond to the PRF of one of the plurality of envelopes.

In some embodiments, the processing device 140 may define that the rate of variation between the PRFs of any two adjacent envelopes of the plurality of envelopes is equal to the limit of PRF acceleration. When two adjacent envelopes of the plurality of envelopes are joined with the limit of PRF acceleration, the acceleration time and the de-acceleration time may occupy the duration of the envelope with a smaller PFR in the two adjacent envelopes.

Figure 7A:
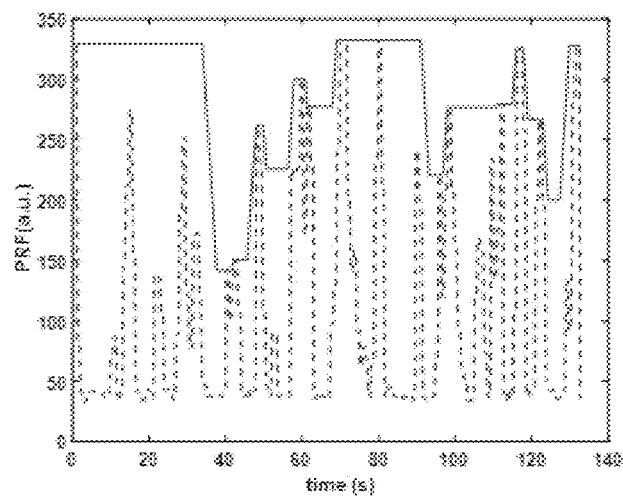
FIGS. 7A-7C are schematic diagrams illustrating exemplary preliminary RF PRFs and updated RF PRFs for three different treatment plans, respectively, according to some embodiments of the present disclosure.
Figure 7B:
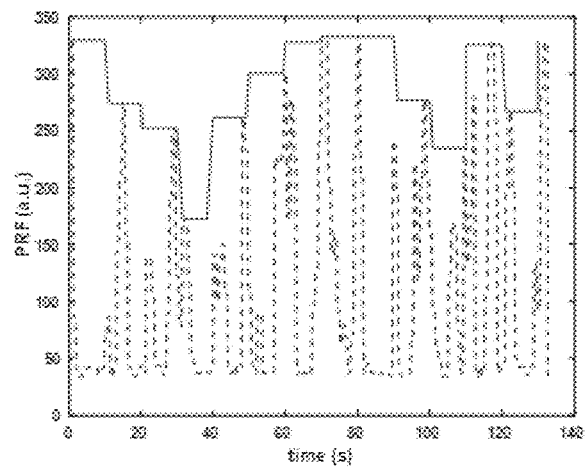
Figure 7C:
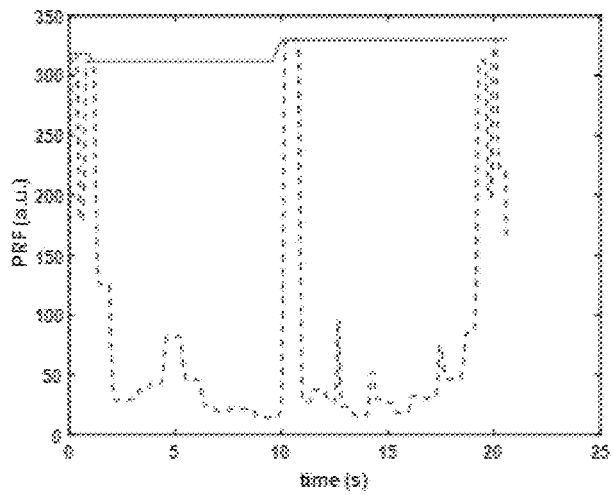

FIGS. 7A-7C are schematic diagrams illustrating exemplary preliminary RF PRFs and updated RF PRFs for three different treatment plans, respectively, according to some embodiments of the present disclosure. As shown in FIGS. 7A-7C, the horizontal axis represents a time range of a treatment plan. The vertical axis represents RF PRF values. The dashed line represents the preliminary RF PRFs in the corresponding treatment plan. The solid line represents the updated RF PRFs determined based on the methods and/or systems for determining updated RF PRFs (e.g., the process 500 and/or the process 600) provided in the present disclosure. As shown in FIGS. 7A-7C, the variation between two adjacent updated RF PRFs is smoother than the variation between two adjacent preliminary RF PRFs.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 8:
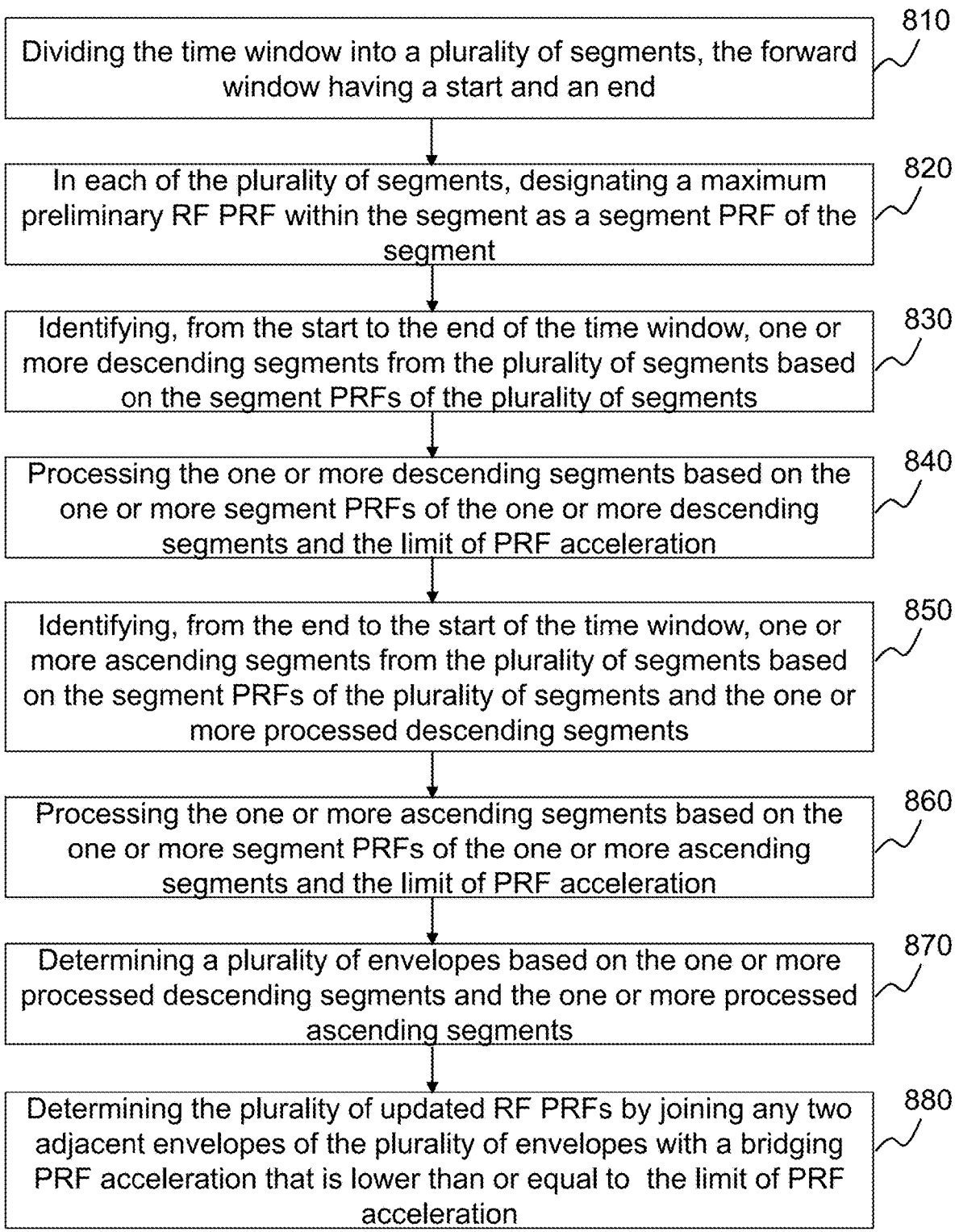
FIG. 8 is a flowchart illustrating an exemplary process for determining a plurality of updated RF PRFs according to some embodiments of the present disclosure.

FIG. 8 is a flowchart illustrating an exemplary process for determining a plurality of updated RF PRFs according to some embodiments of the present disclosure. In some embodiments, the process 800 may be implemented in the system 100 illustrated in FIG. 1. For example, the process 800 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 800 presented below are intended to be illustrative. In some embodiments, the process 800 may be accomplished with one or more additional operations not described, and/or without one or more of the operations discussed. Additionally, the order in which the operations of the process as illustrated in FIG. 8 and described below is not intended to be limiting. In some embodiments, the processing device 140 may perform operation 530 in the process 500 in FIG. 5 based on the process 800.

In 810, the processing device 140 (e.g., the first control module 410 or the updating unit 416) may divide the forward window into a plurality of segments. In some embodiments, the segment may include one preliminary RF PRF, or two or more consecutive preliminary RF PRFs. For example, the processing device 140 may determine one of the treatment sessions in the forward window plan as a segment. As another example, the processing device 140 may combine two or more consecutive treatment sessions in the forward window as a segment. A difference between any two of the preliminary RF PRFs of the two or more consecutive treatment sessions in the segment may be less than a difference threshold.

In 820, the processing device 140 (e.g., the first control module 410 or the updating unit 416) may designate, in each of the plurality of segments, a maximum preliminary RF PRF within the segment as a segment PRF of the segment. In some embodiments, if two or more consecutive segments have a same segment PRF, the processing device 140 may merge the two or more consecutive segments as a single segment.

In some embodiments, the processing device 140 may perform a segment processing operation (e.g., including operations 830-860) to determine whether the rate of variation between the segment PRFs of any two neighboring segments of the plurality of segments in the forward window is larger than the limit of PRF acceleration. In response to a determination that the rate of variation between the segment PRFs of two neighboring segments of the plurality of segments is larger than the limit of PRF acceleration, the processing device 140 may process at least one of the two neighboring segments to make the rate of variation between the two corresponding segment PRFs less than or equal to the limit of PRF acceleration. In response to a determination that the rate of variation between the segment PRFs of two neighboring segments of the plurality of segments is less than or equal to the limit of PRF acceleration, the processing device 140 may retain the two neighboring segments.

In 830, the processing device 140 (e.g., the first control module 410 or the updating unit 416) may identify, from the start to the end of the forward window, one or more descending segments from the plurality of segments in the forward window based on the segment PRFs of the plurality of segments. The segment PRF of the descending segment may be less than the segment PRF of the segment prior to the descending segment.

In 840, the processing device 140 (e.g., the first control module 410 or the updating unit 416) may process the one or more descending segments based on the one or more segment PRFs of the one or more descending segments and the limit of PRF acceleration.

In some embodiments, for each of the one or more descending segments, the processing device 140 may determine a descending PRF based on the limit of PRF acceleration and the segment PRF of the segment prior to the descending segment. In some embodiments, the descending PRF may refer to a value that the segment PRF of the segment prior to the descending segment decreases to at a rate of the limit of PRF acceleration from a start to an end of the descending segment.

The processing device 140 may determine whether the descending PRF is less than the segment PRF of the descending segment. In response to a determination that the descending PRF is less than the segment PRF of the descending segment, the processing device 140 may retain the descending segment. In response to a determination that the descending PRF is larger than or equal to the segment PRF of the descending segment, the processing device 140 may replace the segment PRF of the descending segment with the descending segment.

In some embodiments, the processing device 140 may examine each of the plurality of segments from the start to the end of the forward window based on operations 830-840. For example, because the first segment of the forward window is impossible to be the descending segment, the processing device 140 may perform the examination starting from the second segment. The processing device 140 may determine whether the second segment of the forward window is the descending segment. In response to a determination that the second segment is the descending segment, the processing device 140 may process the second segment based on operation 840. Then the processing device 140 may examine the third segment (e.g., immediately following the second segment) based on the processed second segment. In response to a determination that the second segment is not the descending segment, the processing device 140 may proceed to examine the third segment (e.g., immediately following the second segment) of the forward window. The rest segments may be processed in the same manner until the last segment in the forward window.

In 850, the processing device 140 (e.g., the first control module 410 or the updating unit 416) may identify, from the end to the start of the forward window, one or more ascending segments from the plurality of segments based on the segment PRFs of the plurality of segments and the one or more processed descending segments. The segment PRF of the ascending segment may be less than the segment PRF of the segment immediately following the ascending segment.

In 860, the processing device 140 (e.g., the first control module 410 or the updating unit 416) may process the one or more ascending segments based on the one or more segment PRFs of the one or more ascending segments and the limit of PRF acceleration.

In some embodiments, for each of the one or more ascending segments, the processing device 140 may determine an ascending PRF based on the limit of PRF acceleration and the segment PRF of the segment immediately following the ascending segment. In some embodiments, the ascending PRF may refer to a value that the segment PRF of the segment immediately following the ascending segment decreases to at a rate of the limit of PRF acceleration from an end to a start of the ascending segment.

The processing device 140 may determine whether the ascending PRF is less than the segment PRF of the descending segment. In response to a determination that the ascending PRF is less than the segment PRF of the ascending segment, the processing device 140 may retain the ascending segment. In response to a determination that the ascending PRF is larger than or equal to the segment PRF of the ascending segment, the processing device 140 may replace the segment PRF of the ascending segment with the ascending segment.

In some embodiments, the processing device 140 may examine each of the plurality of segments from the end to the start of the forward window based on operations 850-860. For example, because the last segment of the forward window is impossible to be the ascending segment, the processing device 140 may perform the examination starting from the second segment from last. The processing device 140 may determine whether the second segment from the last of the forward window is the ascending segment. In response to a determination that the second segment from last is the ascending segment, the processing device 140 may process the second segment from last based on operation 860. Then the processing device 140 may examine the third segment from last (e.g., prior to the second segment from last) based on the processed second segment from last. In response to a determination that the second segment from last is not the ascending segment, the processing device 140 may proceed to examine the third segment from last (e.g., prior to the second segment from last) of the forward window. The rest segments may be processed in the same manner until the first segment in the forward window.

In 870, the processing device 140 (e.g., the first control module 410 or the updating unit 416) may determine a plurality of envelopes based on the one or more processed descending segments and the one or more processed ascending segments. In some embodiments, each of the plurality of envelopes may correspond to a processed descending segments or a processed ascending segments.

In 880, the processing device 140 (e.g., the first control module 410 or the updating unit 416) may determine the plurality of updated RF PRFs by joining any two adjacent envelopes of the plurality of envelopes with a bridging PRF acceleration that is lower than or equal to the limit of PRF acceleration.

In some embodiments, the processing device 140 may define that the rate of variation between the PRFs of any two adjacent envelopes of the plurality of envelopes is equal to the limit of PRF acceleration. When two adjacent envelopes of the plurality of envelopes are joined with the limit of PRF acceleration, the acceleration time and the de-acceleration time may occupy the duration of the envelope with a smaller PFR in the two adjacent envelopes. In some embodiments, each of the plurality of updated RF PRFs may correspond to the PRF of one of the plurality of envelopes.

Figure 9:
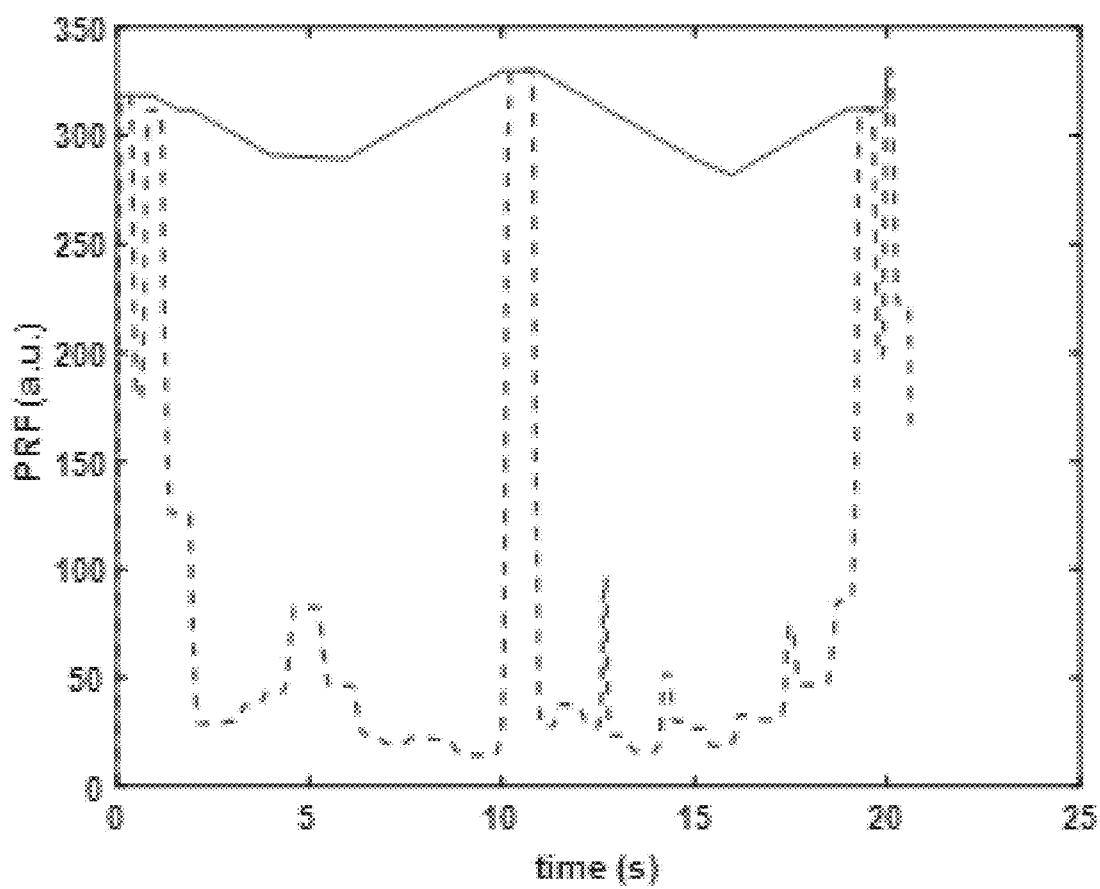
FIG. 9 is a schematic diagram illustrating exemplary preliminary RF PRFs and updated RF PRFs for a treatment plan according to some embodiments of the present disclosure.

FIG. 9 is a schematic diagram illustrating exemplary preliminary RF PRFs and updated RF PRFs for a treatment plan according to some embodiments of the present disclosure. As shown in FIG. 9, the horizontal axis represents a time range of a treatment plan. The vertical axis represents RF PRF values. The dashed line represents the preliminary RF PRFs in the treatment plan. The solid line represents the updated RF PRFs determined based on the methods and/or systems for determining updated RF PRFs (e.g., the process 500 and/or the process 800) provided in the present disclosure. As shown in FIG. 9, the variation of the updated RF PRFs is smoother than the variation of the preliminary RF PRFs.

In some embodiments, when the treatment proceeds to the portion corresponding to the forward window, the processing device 140 (e.g., the first control module 410 or the first control unit 418) may cause the RF source 116 to output electromagnetic waves based on the updated RF PRFs. For example, the processing device 140 may generate an instruction based on the updated RF PRFs. The instruction may indicate a start time and a duration of each updated RF PRF. The instruction may further indicate that the RF source 116 may switch from an updated RF PRF to another updated RF PRF at a rate of variation equal to the limit of PRF acceleration. The instruction may further indicate that the acceleration time and the de-acceleration time may occupy the duration of a smaller updated RF PRF in two adjacent updated RF PRFs. The processing device 140 may cause the RF source 116 to output electromagnetic waves based on the instruction during the forward window.

As another example, the processing device 140 may generate an instruction indicating a curve similar to the solid lines in FIGS. 7A-7C and 9. The processing device 140 may cause the RF source 116 to output electromagnetic waves according to the curve.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

In some embodiments, during a treatment, the processing device 140 may continuously modulate radiation output so that the delivered pulses (e.g., a radiation output rate, a cumulative radiation dose, a pulse repetition frequency (PRF) related to the radiation output, etc.) are consistent with the treatment plan. In general, the RF source 116 may output electromagnetic waves at an RF PRF similar to the modulated or planned radiation PRF. In this case, a difference between two neighboring RF PRFs may be relatively large so that there may be an abrupt output change when the RF source outputs electromagnetic waves at the two neighboring RF PRFs, which may reduce the stability of the RF source. The present disclosure provides systems and/or methods for controlling radiation output so that the change of two neighboring RF PRFs may be relatively smooth during the treatment. The description in connection with FIGS. 10-14 illustrates some embodiments of the systems and/or methods for controlling radiation output provided in the present disclosure.

Figure 10A:
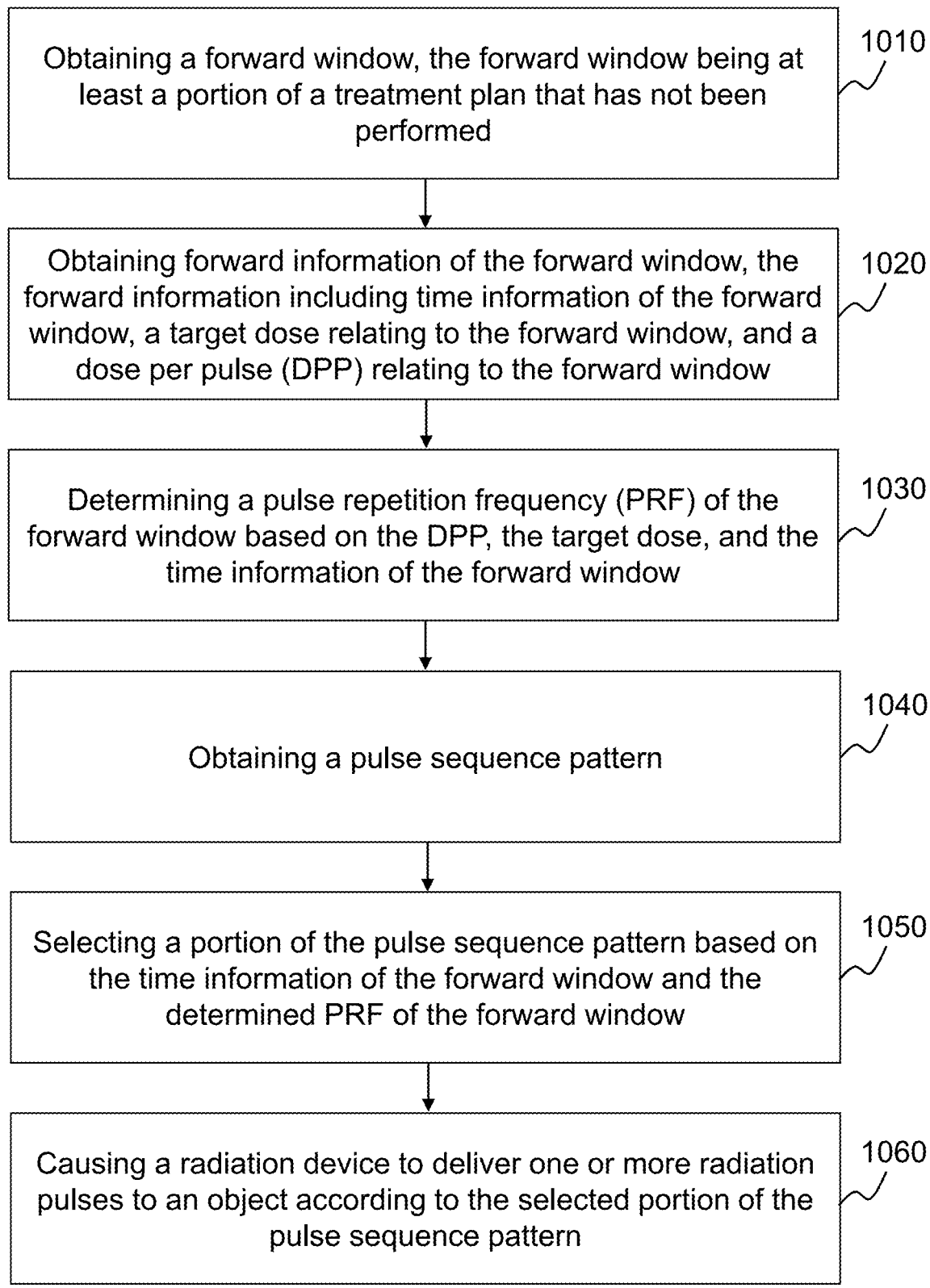
FIG. 10A is a flowchart illustrating an exemplary process for controlling radiation output according to some embodiments of the present disclosure.

FIG. 10A is a flowchart illustrating an exemplary process for controlling radiation output according to some embodiments of the present disclosure. In some embodiments, the process 1000 may be implemented in the system 100 illustrated in FIG. 1. For example, the process 1000 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 1000 presented below are intended to be illustrative. In some embodiments, the process 1000 may be accomplished with one or more additional operations not described, and/or without one or more of the operations discussed. Additionally, the order in which the operations of the process as illustrated in FIG. 10A and described below is not intended to be limiting.

In 1010, the processing device 140 (e.g., the second control module 420 or the second window obtaining unit 421) may obtain a forward window. The forward window may be at least a portion of a treatment plan that has not been performed.

In some embodiments, the forward window may refer to a time window after the current treatment stage. In some embodiments, the processing device 140 may determine the forward window automatically. For example, the processing device 140 may determine the current time as a start time of a forward window and a time point after the current time as the end time of the forward window automatically. The processing device 140 may determine the forward window based on the start time and the end time. In some embodiments, the processing device 140 may determine the forward window based on instructions from a user (e.g., a doctor). For example, the user may input a start time (e.g., the current time) and an end time after the current time through the processing device 140 (e.g., the I/O 230) and/or the terminal 130 (e.g., the I/O 350) and send instructions related to the start time and the end time to the processing device 140. After receiving the instructions, the processing device 140 may determine the forward window based on the start time and the end time.

In 1020, the processing device 140 (e.g., the second control module 420 or the second information obtaining unit 422) may obtain forward information of the forward window. In some embodiments, the processing device 140 may obtain the information related to the treatment plan and obtain the forward information based on the information related to the treatment plan.

The forward information may include time information (e.g., a forward start time of the forward window, a forward end time of the forward window, a forward interval of the forward window, etc.), a forward cumulative radiation dose (also referred to as a target dose) of the forward window, a dose per pulse (DPP) related to the forward window, or the like, or any combination thereof. The forward cumulative radiation dose may refer to a radiation dose delivered in response to a plurality of pulses from the start time of the treatment to the forward end time. In some embodiments, the forward start time or the forward end time may coincide with one of the plurality of control points, or the forward start time and the forward end time may coincide with two of the plurality of control points, respectively, or the forward start time and the forward end time may not coincide with any of the plurality of control points.

The DPP related to the forward window may refer to the DPP in response to one or more pulses that have been delivered during a backward period within the total time of the treatment before the forward window. In some embodiments, when the radiation device 110 delivers pluses during the treatment, the radiation device 110, the processing device 140 or the terminal 130 may record the delivery times at which the pulses are delivered, the cumulative radiation dose that has been delivered, and the number (or count) of pulses that have been delivered, etc. In some embodiments, the processing device 140 may select a backward period as close as possible to the forward window. For example, the end time of the backward period and the start time of the forward window may be the same. The processing device 140 may obtain the actual recorded radiation output and the actual recorded number of pulses in response to one or more pulses that have been delivered during the backward period. The processing device 140 may determine the DPP by dividing the actual recorded radiation output by the actual recorded number of pulses.

The processing device 140 may determine the forward cumulative radiation dose based on the information related to the treatment plan. In some embodiments, there may be a relationship between a time point within the total time of the treatment and a cumulative radiation dose associated with the time point (e.g., indicating a radiation dose from the start time of the treatment to the time point). In some embodiments, the processing device 140 may determine the relationship based on the cumulative radiation doses associated with the control time points related to the treatment plan. In some embodiments, the processing device 140 may determine the relationship by fitting a continuity equation or a discrete equation. In some embodiments, the fitting method may include interpolation, extrapolation, smoothing, regression analysis, the least square method, or the like, or any combination thereof. Exemplary interpolation algorithms may include Lagrange interpolation, Newton interpolation, Hermite interpolation, piecewise interpolation, spline interpolation, linear interpolation, or the like, or a combination thereof. Exemplary extrapolation algorithms may include linear extrapolation, polynomial extrapolation, conic extrapolation, French curve extrapolation, linear predictors, Kalman filtering, extended Kalman filtering, neural-network predictors, or the like, or a combination thereof. Exemplary techniques for a regression analysis may include linear regression, nonlinear regression, multiple regression, logistic regression, partial regression, or the like, or a combination thereof. With the determined relationship (e.g., a planned cumulative radiation function), the processing device 140 may determine a cumulative radiation dose associated with any time point within the total time of the treatment. For example, if the forward end time coincides with a control point, the processing device 140 may determine the forward cumulative radiation dose based on the cumulative radiation dose associated with the control point in the treatment plan. As another example, if the forward end time does not coincide with any control points, the processing device 140 may determine the forward cumulative radiation dose based on the planned cumulative radiation function.

In 1030, the processing device 140 (e.g., the second control module 420 or the PRF determination unit 423) may determine a pulse repetition frequency (PRF) of the forward window based on the DPP, the target dose, and the time information of the forward window.

A forward radiation dose may refer to a radiation dose delivered in response to one or more pulses during the forward interval of the forward window. The processing device 140 may determine the forward radiation dose based on the forward cumulative radiation dose. In some embodiments, the processing device 140 may determine the forward radiation dose by subtracting a cumulative radiation dose associated with the forward start time (e.g., the current time) from a cumulative radiation dose associated with the forward end time (e.g., the forward cumulative radiation dose). In a condition that the forward start time is equal to the current time, the processing device 140 may determine the cumulative radiation dose of the current time (e.g., an actually recorded radiation dose delivered in response to one or more pulses that have been transmitted during a time period from the start time of the treatment to the current time) as the cumulative radiation dose associated with the forward start time. In a condition that the forward start time is later than the current time (e.g., a time when the radiation device 110 finishes delivering a radiation pulse and now is about to deliver another radiation pulse), the processing device 140 may determine the cumulative radiation dose associated with the forward start time based on the planned cumulative radiation function.

In some embodiments, the processing device 140 may determine the number of pulses delivered during the forward interval by dividing the forward radiation dose by the DPP. The processing device 140 may determine the PRF of the forward window by dividing the number of pulses delivered during the forward interval by the forward interval.

In 1040, the processing device 140 (e.g., the second control module 420 or the pattern obtaining unit 424) may obtain a pulse sequence pattern. The pulse sequence pattern may include a plurality of pulse sequences during a period of time. Each of the plurality of pulse sequences may correspond to a specific PRF. Each of the plurality of pulse sequences may include a plurality of pulses and a generation time of each of the plurality of pulses. In some embodiments, each of the plurality of pulse sequences may further include an RF PRF and an electron PRF that facilitate the pulses delivered according to the pulse sequence.

Figure 10B:
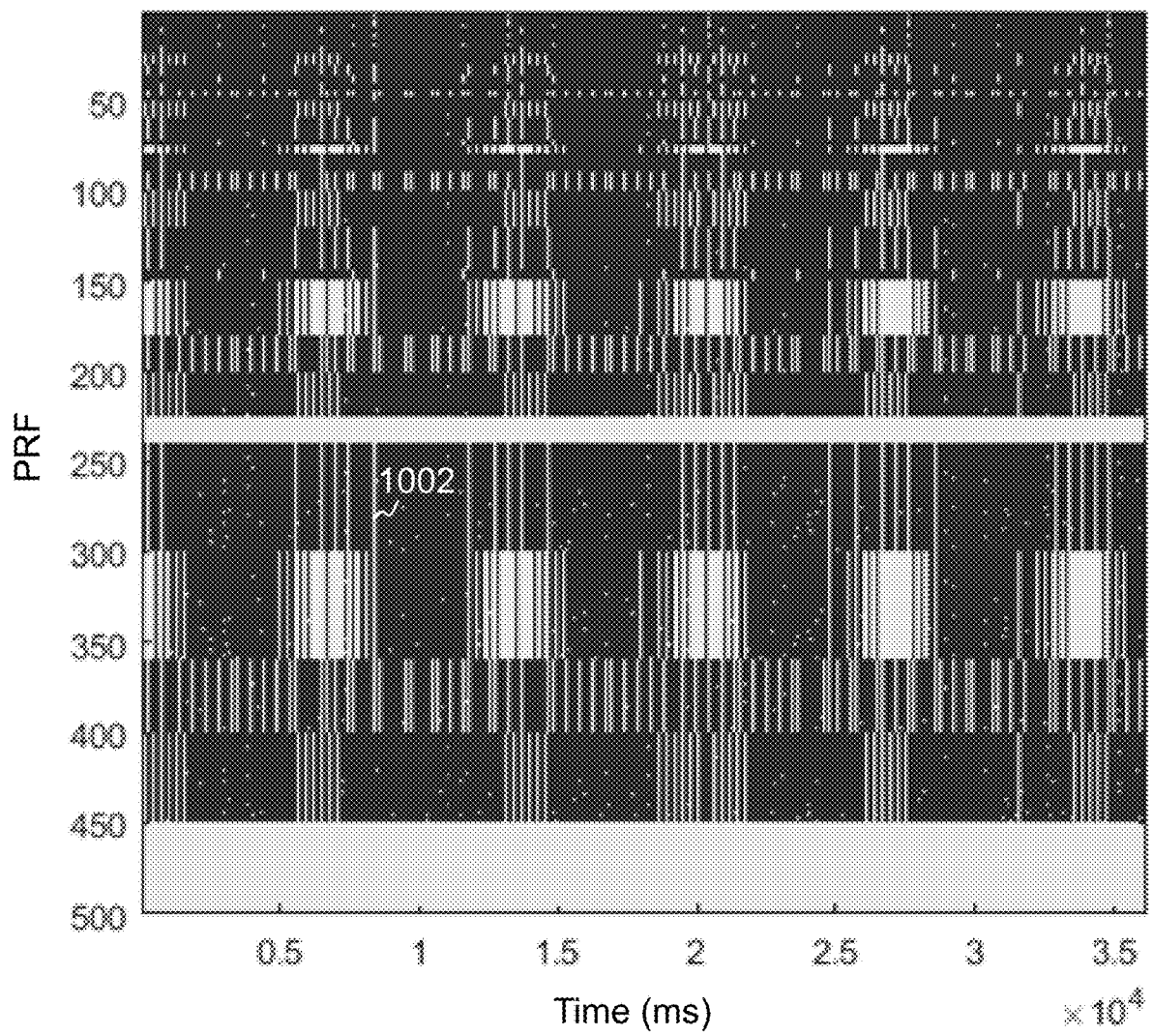
FIG. 10B is a schematic diagram illustrating exemplary pulse sequence pattern used in a process for radiation output control according to some embodiments of the present disclosure.

FIG. 10B is a schematic diagram illustrating an exemplary pulse sequence pattern used in a process for radiation output control according to some embodiments of the present disclosure. As shown in FIG. 10B, the horizontal axis of the pulse sequence pattern 1001 represents a time range, and the vertical axis of the pulse sequence pattern 1001 represents PRF values. In the pulse sequence pattern 1001, the gray area represents that there is at least one pulse generated at the corresponding time. For example, as shown in the pulse sequence pattern 1001, according to the horizontal and the vertical axes, there may be a plurality of pulse sequences each of which corresponds to a PRF value in the range of 250 Hz-400 Hz. In these pulse sequences, there may be a pulse (e.g., represented as the gray area 1002 in FIG. 10B) generated at the eighth second in a process with a duration of 35 seconds.

In the pulse sequence pattern 1001, the gray area represents that during the times corresponding to the gray area, the electromagnetic waves and the electrons are injected into the acceleration structure 112 synchronously so that pulses are generated. The black area represents that during the times corresponding to the black area, the injection of the electromagnetic waves and the electrons into the acceleration structure 112 are out of sync so that no pulses are generated.

In 1050, the processing device 140 (e.g., the second control module 420 or the selection unit 425) may select a portion of the pulse sequence pattern based on the time information of the forward window and the determined PRF of the forward window. For example, the total time of the treatment is 35 seconds. The forward interval of the forward window is 40-80 ms within the total time. The PRF of the forward window determined in operation 1030 is 150 Hz. The processing device 140 may select a portion of the pulse sequence pattern 1001 in FIG. 10B corresponding to 150 Hz and a time period of 40-80 ms.

In 1060, the processing device 140 (e.g., the second control module 420 or the second control unit 426) may cause the radiation device 110 to deliver one or more radiation pulses to an object according to the selected portion of the pulse sequence pattern.

In some embodiments, the processing device 140 may cause the electron gun 114 to inject electrons into the acceleration structure 112 at an electron frequency corresponding to the selected portion of the pulse sequence pattern. The processing device 140 may cause the RF source 116 to inject electromagnetic waves into the acceleration structure 112 at an RF PRF corresponding to the selected portion of the pulse sequence pattern. The processing device 140 may cause the acceleration structure 112 to deliver, based on the injected electrons and the electromagnetic waves, the one or more radiation pulses to the object.

In some embodiments, during the treatment, the processing device 140 may determine a plurality of forward windows and modulate radiation output in each forward window so that the delivered pulses (e.g., a radiation output rate, a cumulative radiation dose, a pulse repetition frequency (PRF), etc.) are consistent with the treatment plan by repeating the process 1000. The intervals of the plurality of forward windows may be the same (e.g., 4 ms) or different.

In some embodiments, during the modulation of radiation output in the treatment, the operation of causing the radiation device 110 to deliver pulses to the object based on the pulse sequence pattern may make the RF source 116 output electromagnetic waves whose RF PRFs vary smoothly. For example, a difference between any two adjacent RF PRFs of the smoothly varied RF PRFs may be less than a difference threshold. As another example, a rate of variation between any two adjacent RF PRFs of the smoothly varied RF PRFs may be less than a rate threshold. As still another example, during the modulation of radiation output in the treatment, the processing device 140 may obtain a RF PRF related to the forward window based on the pulse sequence pattern at the present time. A difference between the RF PRF and a prior RF PRF (e.g., a last RF PRF) that have been performed by the RF source 116 is less than the difference threshold. In this way, the stability of the RF source 116 may be improved.

In some embodiments, different treatment plans may share a same pulse sequence pattern. In some embodiments, different treatment plans may have their own pulse sequence pattern.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 11:
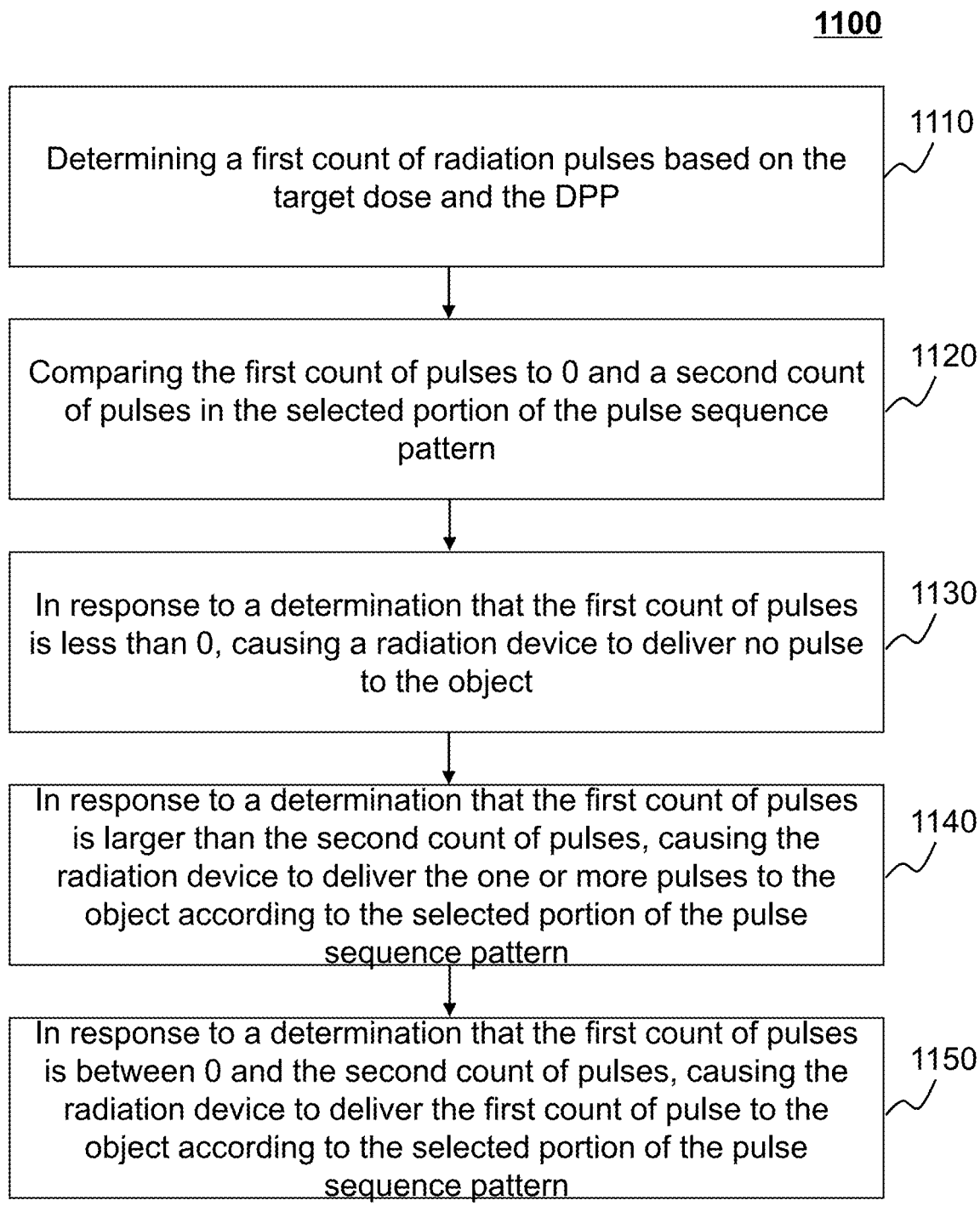
FIG. 11 is a flowchart illustrating an exemplary process for causing an acceleration structure to deliver one or more radiation pulses to an object based on a selected portion of a pulse sequence pattern according to some embodiments of the present disclosure.

FIG. 11 is a flowchart illustrating an exemplary process for causing a radiation device to deliver one or more radiation pulses to an object based on a selected portion of a pulse sequence pattern according to some embodiments of the present disclosure. In some embodiments, the process 1100 may be implemented in the system 100 illustrated in FIG. 1. For example, the process 1100 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 1100 presented below are intended to be illustrative. In some embodiments, the process 1100 may be accomplished with one or more additional operations not described, and/or without one or more of the operations discussed. Additionally, the order in which the operations of the process as illustrated in FIG. 11 and described below is not intended to be limiting. In some embodiments, the processing device 140 may perform operation 1060 of the process 1000 in FIG. 10A based on the process 1100.

In 1110, the processing device 140 (e.g., the second control module 420 or the second control unit 426) may determine a first count of radiation pulses (also referred to as the number of pulses of the forward window) based on the target dose and the DPP. Details regarding the determination of the first count may be found elsewhere in the present disclosure (e.g., the description in connection with operation 1030 in FIG. 10).

In 1120, the processing device 140 (e.g., the second control module 420 or the second control unit 426) may compare the first count of pulses to 0 and a second count of pulses in the selected portion of the pulse sequence pattern.

In 1130, in response to a determination that the first count of pulses is less than 0, the processing device 140 (e.g., the second control module 420 or the second control unit 426) may cause the radiation device 110 to deliver no pulse to the object.

In 1140, in response to a determination that the first count of pulses is larger than the second count of pulses, the processing device 140 (e.g., the second control module 420 or the second control unit 426) may cause the radiation device 110 to deliver the one or more pulses to the object according to the selected portion of the pulse sequence pattern.

In 1150, in response to a determination that the first count of pulses is between 0 and the second count of pulses, the processing device 140 (e.g., the second control module 420 or the second control unit 426) may cause the radiation device 110 to deliver the first count of pulses to the object according to the selected portion of the pulse sequence pattern. For example, the first count is equal to 2, and there are 3 pulses in the selected portion of the pulse sequence pattern. The processing device 140 may cause the radiation device 110 to deliver 2 pulses to the object according to the first two pulses in the selected portion of the pulse sequence pattern.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, in response to a determination that the first count of pulses is equal to 0, the processing device 140 may cause the radiation device 110 to deliver no pulse to the object. As another example, in response to a determination that the first count of pulses is equal to the second count of pulses, the processing device 140 may cause the radiation device 110 to deliver the one or more pulses to the object according to the selected portion of the pulse sequence pattern.

Figure 12:
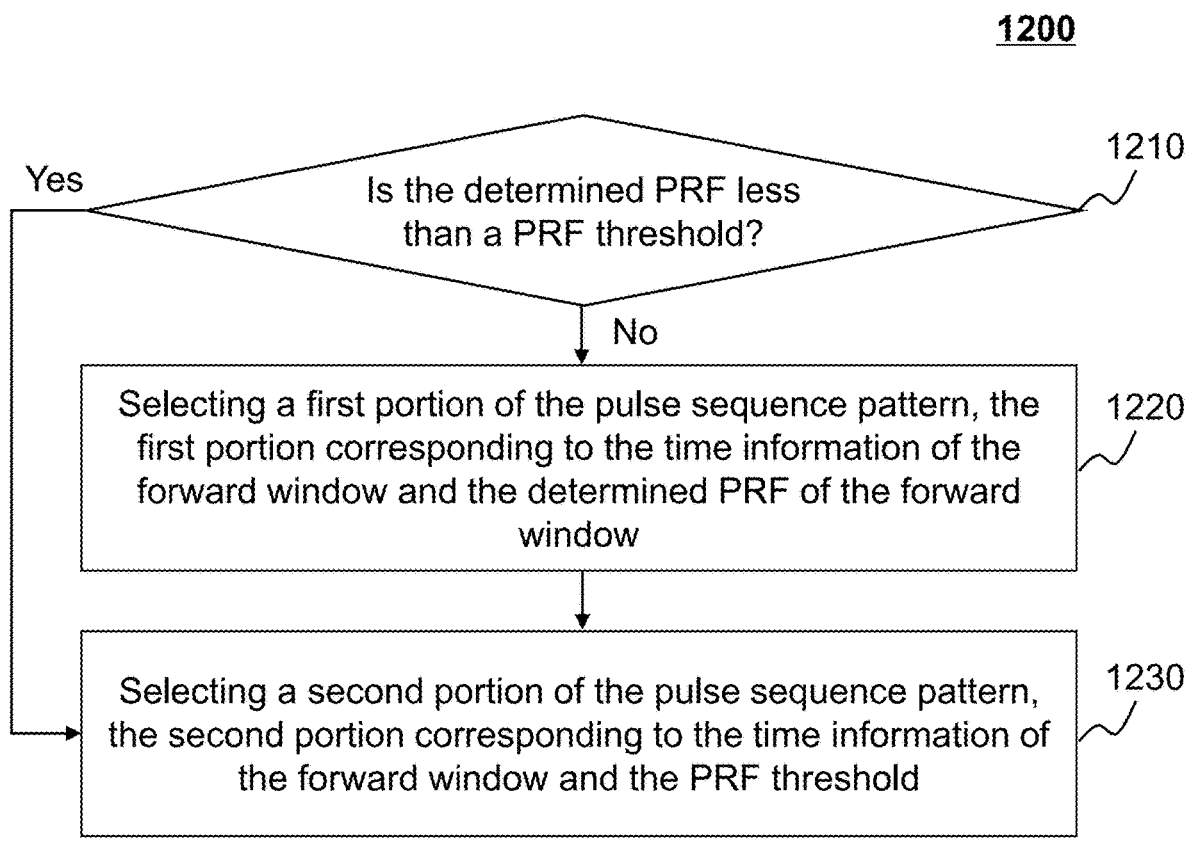
FIG. 12 is a flowchart illustrating an exemplary process for selecting a portion of a pulse sequence pattern according to some embodiments of the present disclosure.

FIG. 12 is a flowchart illustrating an exemplary process for selecting a portion of a pulse sequence pattern according to some embodiments of the present disclosure. In some embodiments, the process 1200 may be implemented in the system 100 illustrated in FIG. 1. For example, the process 1200 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 1200 presented below are intended to be illustrative. In some embodiments, the process 1200 may be accomplished with one or more additional operations not described, and/or without one or more of the operations discussed. Additionally, the order in which the operations of the process as illustrated in FIG. 12 and described below is not intended to be limiting. In some embodiments, the processing device 140 may perform operation 1050 of the process 1000 in FIG. 10A based on the process 1200.

In 1210, the processing device 140 (e.g., the second control module 420 or the selection unit 425) may determine whether the determined PRF (e.g., the PRF determined in operation 1030 of the process 1000 in FIG. 10A) is less than a PRF threshold.

In response to a determination that the determined PRF is greater than the PRF threshold, the process 1200 may proceed to operation 1220 in which the processing device 140 may select a first portion of the pulse sequence pattern. The first portion may correspond to the time information of the forward window and the determined PRF of the forward window.

In response to a determination that the determined PRF is less than the PRF threshold, the process 1200 may proceed to operation 1230 in which the processing device 140 may select a second portion of the pulse sequence pattern. The second portion may correspond to the time information of the forward window and the PRF threshold.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, in response to a determination that the determined PRF is equal to the PRF threshold, the process 1200 may proceed to operation 1220 or 1230.

Figure 13:
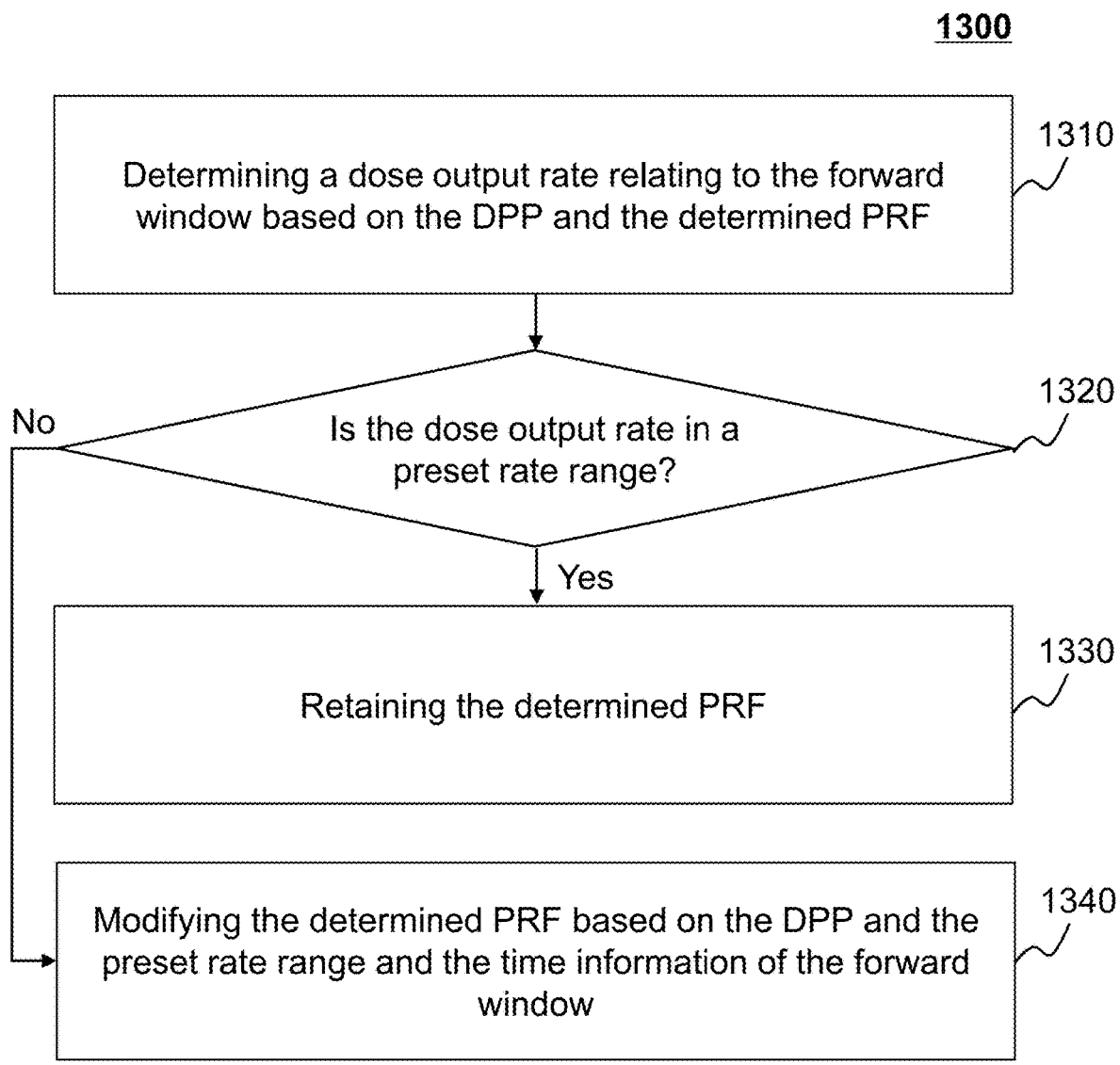
FIG. 13 is a flowchart illustrating an exemplary process for determining a PRF of a forward window according to some embodiments of the present disclosure.

FIG. 13 is a flowchart illustrating an exemplary process for determining a PRF of a forward window according to some embodiments of the present disclosure. In some embodiments, the process 1300 may be implemented in the system 100 illustrated in FIG. 1. For example, the process 1300 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 1300 presented below are intended to be illustrative. In some embodiments, the process 1300 may be accomplished with one or more additional operations not described, and/or without one or more of the operations discussed. Additionally, the order in which the operations of the process as illustrated in FIG. 13 and described below is not intended to be limiting.

In some embodiments, the forward information may further include a preset rate range of a dose output rate during each treatment session within the total time of the treatment. The dose output rate in response to radiation pulses delivered in a treatment session may be within the corresponding preset rate range.

After the processing device 140 performs operation 1030 of the process 1000 in FIG. 10A, the processing device 140 may perform the process 1300 to modify the PRF determined in operation 1030 based on the preset rate range to make the dose output rate of the forward window within the corresponding preset rate range.

In 1310, the processing device 140 (e.g., the second control module 420 or the PRF determination unit 423) may determine a dose output rate relating to the forward window based on the DPP and the determined PRF. In some embodiments, the processing device 140 may determine the dose output rate relating to the forward window by determining a product of the DPP and the determined PRF.

In 1320, the processing device 140 (e.g., the second control module 420 or the PRF determination unit 423) may determine whether the dose output rate is in the preset rate range. In response to a determination that the dose output rate is in the preset rate range, the process 1300 may proceed to operation 1330 in which the processing device 140 may retain the determined PRF. In response to a determination that the dose output rate is outside the preset rate range, the process 1300 may proceed to operation 1340 in which the processing device 140 may modify the determined PRF based on the DPP and the preset rate range of the forward window. In some embodiments, the processing device 140 may determine the modified PRF by dividing a PRF value (e.g., the minimum PRF value or the maximum PRF value) in the preset rate range by the DPP.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 14:
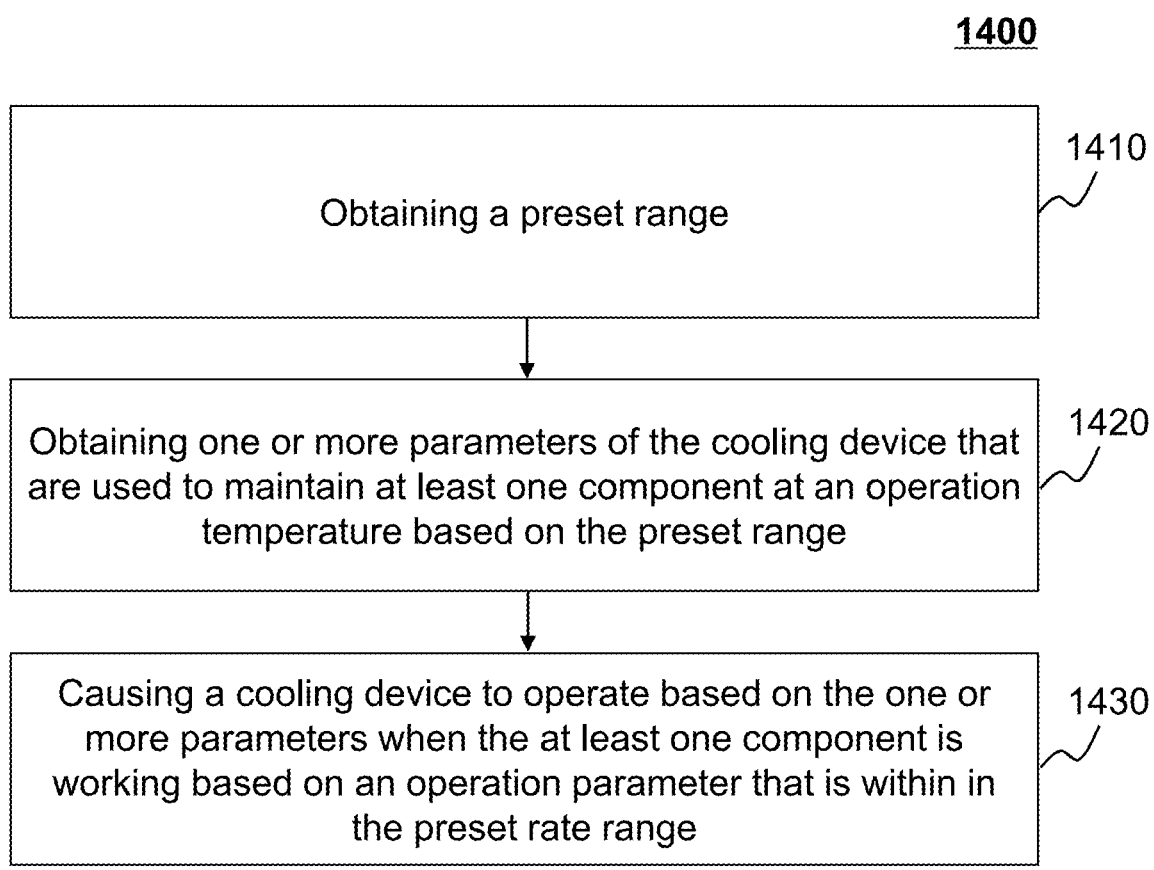
FIG. 14 is a flowchart illustrating an exemplary process for controlling a cooling device according to some embodiments of the present disclosure.

FIG. 14 is a flowchart illustrating an exemplary process for controlling a cooling device according to some embodiments of the present disclosure. In some embodiments, the process 1400 may be implemented in the system 100 illustrated in FIG. 1. For example, the process 1400 may be stored in a storage medium (e.g., the storage device 150, the storage 220 of the processing device 140, the storage 390 of the terminal 130, the memory 360 of the terminal 130, etc.) as a form of instructions, and invoked and/or executed by the processing device 140 (e.g., the processor 210 of the processing device 140, or one or more modules or units in the processing device 140 illustrated in FIG. 4) and/or the terminal 130 (e.g., the CPU 340 of the terminal 130, or the GPU 330 of the terminal 130). The operations of the illustrated process 1400 presented below are intended to be illustrative. In some embodiments, the process 1400 may be accomplished with one or more additional operations not described, and/or without one or more of the operations discussed. Additionally, the order in which the operations of the process as illustrated in FIG. 14 and described below is not intended to be limiting.

In some embodiments, when the radiation device 110 works based on different operation parameters, e.g., the radiation device 110 delivers pulses at different dose output rates or different radiation PRFs, and/or the RF source 116 provides electromagnetic waves at different RF PRFs, the power consumption and the resulting heat may be different, thereby leading to different temperatures of the radiation device 110. The cooling device 118 may be configured to protect the radiation device 110 from overheating by circulating a coolant (e.g., cooling water) to the at least one component (e.g., the acceleration structure 112, the electron gun 114, or the RF source 116) in the radiation device 110.

When the treatment proceeds to a control point after which a preset range of the operation parameter will be changed, the processing device 140 may perform the process 1400 to adjust the cooling device 118 to stabilize the temperature of the radiation device 110 when the radiation device 110 works based on the operation parameter within the changed preset range in the subsequent treatment stage.

In 1410, the processing device 140 (e.g., the second control module 420 or the second control unit 426) may obtain a preset range of an operation parameter of the radiation device 110. In some embodiments, the preset range of the operation parameter of the radiation device 110 may include a preset range of dose output rates, a preset range of RF PRFs, a preset range of radiation PRFs, or the like, or any combination thereof.

In 1420, the processing device 140 (e.g., the second control module 420 or the second control unit 426) may obtain one or more parameters of the cooling device 118 that are used to maintain at least one component of the radiation output control system 100 at an operation temperature based on the preset range. The at least one component of the radiation output control system 100 may include at least one of the acceleration structure 112, the electron gun 114, and the RF source 116. The one or more parameters of the cooling device 118 may include the temperature of the coolant, the flow velocity of the coolant, a start time to adjust the cooling device 118 based on the preset range, or the like. The operation temperature may be a specific value or a value range in which the at least one component may have good performance in the course of running.

The processing device 140 may determine the one or more parameters of the cooling device 118 based on the power consumption and the resulting heat of the at least one component related to the preset range, the operation temperature, and the relation of the operation temperature, the one or more parameters, the power consumption, the resulting heat, and the preset range. The relation may be determined in advance and be stored in the storage medium (e.g., the storage device 150, the storage 220 of the processing device 140, the storage 390 of the terminal 130, the memory 360 of the terminal 130, etc.) of the radiation output control system 100.

In 1430, the processing device 140 (e.g., the second control module 420 or the second control unit 426) may cause the cooling device 118 to operate based on the one or more parameters when the at least one component is working based on the operation parameter that is within in the preset range.

Figure 15:
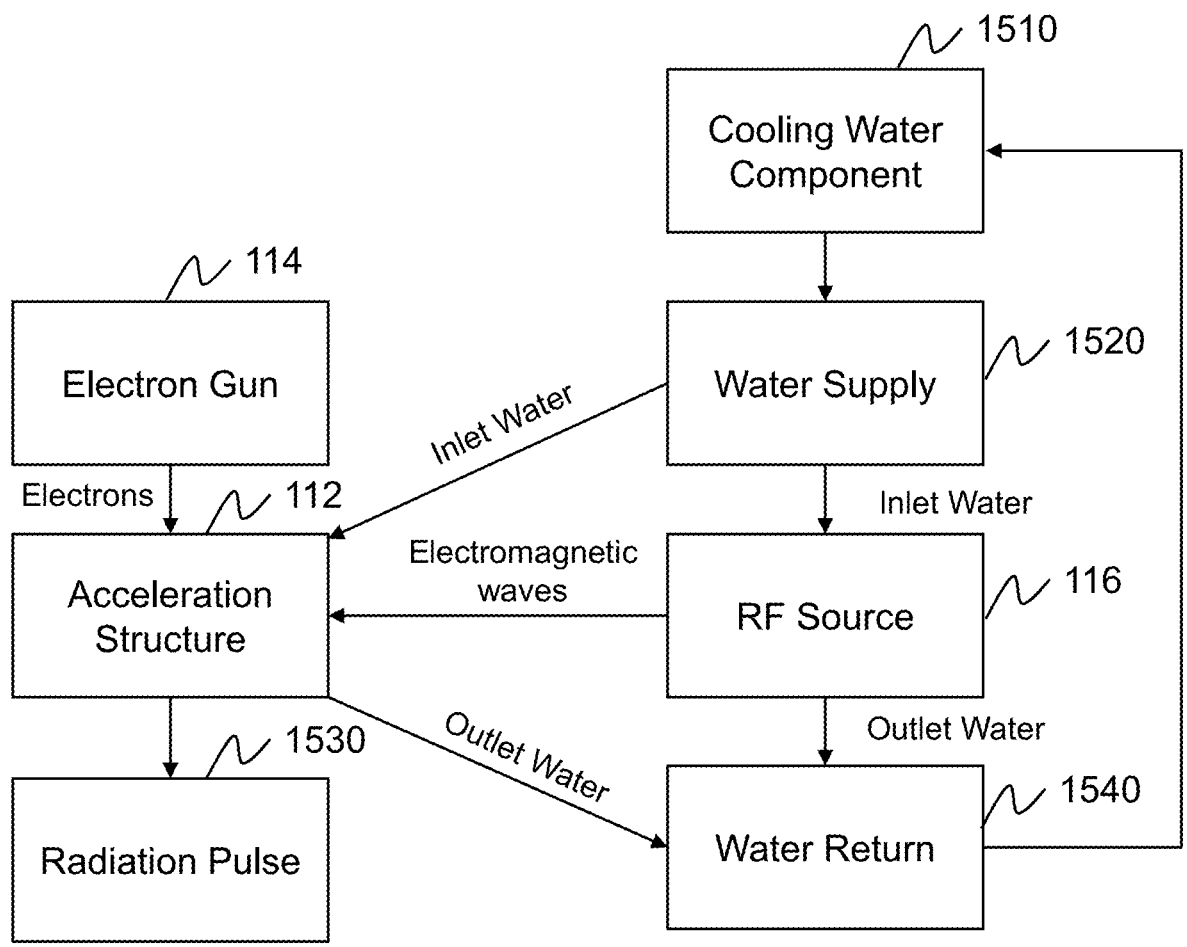
FIG. 15 is a schematic diagram illustrating an exemplary workflow of the cooling device according to some embodiments of the present disclosure.

FIG. 15 is a schematic diagram illustrating an exemplary workflow of the cooling device 118 according to some embodiments of the present disclosure. As shown in FIG. 15, the acceleration structure 112 may provide radiation pulses 1530. The electron gun 114 may inject electrons into the acceleration structure 112 at the electron RPF. The RF source 116 may inject electromagnetic waves (e.g., microwave pulses) into the acceleration structure 112 at the RF PRF to accelerate the electrons to generate the radiation pulses 1530.

As shown in FIG. 15, the cooling water component 1510 in the cooling device 118 may be configured to be adaptive according to inlet water temperature. The water supply component 1520 in the cooling device 118 may vary the water flow of the inlet water and introduce the inlet water into the acceleration structure 112 and/or the RF source 116. The outlet water from the acceleration structure 112 and/or the RF source 116 may return back to the cooling water component 1510. For example, the water return component 1540 in the cooling device 118 may facilitate the return of the outlet water to the cooling water component 1510.

The water temperature and the water flow of the inlet water may affect the cooling response (or cooling performance) of the radiation device 110. Considering that the operation parameter of the treatment plan (e.g., the magnetron PRF trajectory, the dose rate of each treatment stage, etc.) has been preset, the total heat that needs to be dissipated to the radiation device 110 (e.g., the acceleration structure 112 and/or and the RF source 116) may also be predicted. Thus, when the treatment proceeds to a control point after which a preset range of the operation parameter needs to be changed according to the treatment plan, pre-tuning the cooling water temperature and/or the water flow may accelerate the re-balance process, thereby achieving a more stable operation of the radiation device 110. The start time to adjust the cooling water temperature and/or the water flow may be determined based on the preset range and the cooling response of the radiation device 110.

It is understood that in the description of FIG. 15, water is exemplified here as a coolant for illustration purposes and not intended to be limiting. Other medium may be used as a coolant in the cooling device 118 as disclosed herein. Exemplary coolants may include liquid coolants (e.g., water), gas coolants (e.g., cold air), or the like.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A system, comprising:
   one or more storage devices comprising a set of instructions; and
   one or more processors configured to communicate with the one or more storage devices, wherein when executing the set of instructions, the one or more processors are directed to cause the system to perform operations including:
      identifying a time window of a procedure;
      obtaining operational information of the time window, the operational information including a limit of pulse repetition frequency (PRF) acceleration and a plurality of preliminary radio frequency (RF) pulse repetition frequencies (PRFs);
      determining a plurality of updated RF PRFs by updating the plurality of preliminary RF PRFs, a rate of variation between any two adjacent updated RF PRFs being less than or equal to the limit of PRF acceleration; and
      causing an RF source to generate electromagnetic waves at the plurality of updated RF PRFs in the time window.

2. The system of claim 1, wherein the determining the plurality of updated RF PRFs by updating the plurality of preliminary RF PRFs includes:
   dividing the forward window into a plurality of segments;
   in each of the plurality of segments, designating a maximum preliminary RF PRF within the segment as a segment PRF of the segment; and
   determining the plurality of updated RF PRFs by joining, based on the segment PRFs of the plurality of segments, any two adjacent segments of the plurality of segments with a bridging PRF acceleration that is lower than or equal to the limit of PRF acceleration.

3. The system of claim 2, wherein the operational information of the time window further includes a minimum duration of an RF PRF.

4. The system of claim 3, wherein the determining the plurality of updated RF PRFs by joining any two adjacent segments of the plurality of segments with the bridging PRF acceleration that is lower than or equal to the limit of PRF acceleration includes:
   identifying one or more valley segments from the plurality of segments, wherein for each of the one or more valley segments, the segment PRF of the valley segment is less than the segment PRFs of valley adjacent segments of the valley segment, the valley adjacent segments and the valley segment being three consecutive segments in the forward window with the valley segment in the middle;
   processing the one or more valley segments based on the one or more segment PRFs corresponding to the one or more valley segments, the limit of PRF acceleration, and the minimum duration of an RF PRF;
   identifying one or more intermediate segments from the plurality of segments, wherein for each of the one or more intermediate segments, the segment PRF of the intermediate segment is less than the segment PRF of only one of one or more intermediate adjacent segments of the intermediate segment, the one or more intermediate adjacent segments and the intermediate segment being three consecutive segments in the forward window with the intermediate segment in the middle or two consecutive segments in the forward window;
   processing the one or more intermediate segments based on the one or more segment PRFs of the one or more intermediate segments, the limit of PRF acceleration, and the minimum duration of an RF PRF;
   determining a plurality of envelopes based on the one or more processed valley segments and the one or more processed intermediate segments; and
   determining the plurality of updated RF PRFs by joining any two adjacent envelopes of the plurality of envelopes with the bridging PRF acceleration that is lower than or equal to the limit of PRF acceleration.

5. The system of claim 4, wherein the processing the one or more valley segments based on the one or more segment PRFs corresponding to the one or more valley segments, the limit of PRF acceleration, and the minimum duration of an RF PRF includes:
   for each of the one or more valley segments,
      determining a first sum of a de-acceleration time of the valley segment, an acceleration time of the valley segment, and the minimum duration of an RF PRF;

determining whether the first sum is shorter than a segment time of the valley segment;

in response to a determination that the first sum is shorter than the segment time of the valley segment, retaining the valley segment; and in response to a determination that the first sum is longer than the segment time of the valley segment, merging the valley segment with a first adjacent segment of the valley adjacent segments by increasing the segment PRF of the valley segment to the segment PRF of the first adjacent segment, the segment PRF of the first adjacent segment being less than the segment RPF of a second adjacent segment of the valley adjacent segments.

6. The system of claim 5, wherein the processing the one or more valley segments based on the one or more segment PRFs corresponding to the one or more valley segments, the limit of PRF acceleration, and the minimum duration of an RF PRF further includes:

for each of the one or more valley segments,
determining a first difference between the segment PRF of the segment prior to the valley segment and the segment PRF of the valley segment;
determining the de-acceleration time based on the first difference and the limit of PRF acceleration;
determining a second difference between the segment PRF of the segment immediately following the valley segment and the segment PRF of the valley segment; and
determining the acceleration time based on the second difference and the limit of PRF acceleration.

7. The system of claim 4, wherein the processing the one or more intermediate segments based on the one or more segment PRFs corresponding to the one or more intermediate segments, the limit of PRF acceleration, and the minimum duration of an RF PRF includes:

for each of the one or more intermediate segments,
determining a second sum of a de-acceleration time or an acceleration time of the intermediate segment plus the minimum duration of an RF PRF;
determining whether the second sum is shorter than a segment time of the intermediate segment;
in response to a determination that the second sum is shorter than the segment time of the intermediate segment, retaining the intermediate segment; and
in response to a determination that the second sum is longer than the segment time of the intermediate segment, merging the intermediate segment with a third adjacent segment of the one or more intermediate adjacent segments by increasing the segment PRF of the intermediate segment to the segment PRF of the third adjacent segment, the segment PRF of the third adjacent segment being larger than the segment RPF of the intermediate segment.

8. The system of claim 7, wherein the processing the one or more intermediate segments based on the one or more segment PRFs corresponding to the one or more intermediate segments, the limit of PRF acceleration, and the minimum duration of an RF PRF further includes:

for each of the one or more intermediate segments,
determining a third difference between the segment PRF of the third adjacent segment and the segment PRF of the intermediate segment; and
determining the de-acceleration time or the acceleration time based on the third difference and the limit of PRF acceleration.

9. The system of claim 2, wherein the time window includes a start and an end; and wherein the determining the plurality of updated RF PRFs by joining any two adjacent segments of the plurality of segments with the bridging PRF acceleration that is lower than or equal to the limit of PRF acceleration includes:

identifying, from the start to the end of the time window, one or more descending segments from the plurality of segments based on the segment PRFs of the plurality of segments, wherein for each of the one or more descending segments, the segment PRF of the descending segment is less than the segment PRF of the segment prior to the descending segment;

processing the one or more descending segments based on the one or more segment PRFs of the one or more descending segments and the limit of PRF acceleration;

identifying, from the end to the start of the time window, one or more ascending segments from the plurality of segments based on the segment PRFs of the plurality of segments and the one or more processed descending segments, wherein for each of the one or more ascending segments, the segment PRF of the ascending segment is less than the segment PRF of the segment immediately following the ascending segment;

processing the one or more ascending segments based on the one or more segment PRFs of the one or more ascending segments and the limit of PRF acceleration;

determining a plurality of envelopes based on the one or more processed descending segments and the one or more processed ascending segments; and determining the plurality of updated RF PRFs by joining any two adjacent envelopes of the plurality of envelopes with the bridging PRF acceleration that is lower than or equal to the limit of PRF acceleration.

10. The system of claim 9, wherein the processing the one or more descending segments based on the one or more segment PRFs of the one or more descending segments and the limit of PRF acceleration includes:

for each of the one or more descending segments,
determining a descending PRF based on the limit of PRF acceleration and the segment PRF of the segment prior to the descending segment, wherein the descending PRF refers to a value that the segment PRF of the segment prior to the descending segment decreases to at a rate of the limit of PRF acceleration from a start to an end of the descending segment;
determining whether the descending PRF is less than the segment PRF of the descending segment;
in response to a determination that the descending PRF is less than the segment PRF of the descending segment, retaining the descending segment; and
in response to a determination that the descending PRF is larger than the segment PRF of the descending segment, replacing the segment PRF of the descending segment with the descending segment.

11. The system of claim 9, wherein the processing the one or more ascending segments based on the one or more segment PRFs of the one or more ascending segments and the limit of PRF acceleration includes:

for each of the one or more ascending segments,
determining an ascending PRF based on the limit of PRF acceleration and the segment PRF of the segment immediately following the ascending segment, wherein the ascending PRF refers to a value that the segment PRF of the segment immediately following the ascending segment decreases to at a rate of the limit of PRF acceleration from an end to a start of the ascending segment;

determining whether the ascending PRF is less than the segment PRF of the descending segment;

in response to a determination that the ascending PRF is less than the segment PRF of the ascending segment, retaining the ascending segment; and in response to a determination that the ascending PRF is larger than the segment PRF of the ascending segment, replacing the segment PRF of the ascending segment with the ascending PRF.

12. The system of claim 1, wherein
the procedure is a treatment by radiation, and
the time window of the procedure is a forward window corresponding to at least a portion of a treatment that has not been performed.

13. A system for controlling radiation output, comprising:
one or more storage devices comprising a set of instructions; and
one or more processors configured to communicate with the one or more storage devices, wherein when executing the set of instructions, the one or more processors are directed to cause the system to perform operations including:
  obtaining a forward window, the forward window being at least a portion of a treatment plan that has not been performed;
  obtaining forward information of the forward window, the forward information including time information of the forward window, a target dose relating to the forward window, and a dose per pulse (DPP) relating to the forward window;
  determining a pulse repetition frequency (PRF) of the forward window based on the DPP, the target dose, and the time information of the forward window;
  obtaining a pulse sequence pattern, wherein the pulse sequence pattern includes a plurality of pulse sequences during a period of time, each of the plurality of pulse sequences corresponding to a specific PRF, each of the plurality of pulse sequences including a plurality of pulses and a generation time of each of the plurality of pulses;
  selecting a portion of the pulse sequence pattern based on the time information of the forward window and the determined PRF of the forward window; and
  causing a radiation device to deliver one or more radiation pulses to an object according to the selected portion of the pulse sequence pattern.

14. The system of claim 13, wherein the causing the radiation device to deliver the one or more pulses to the object according to the selected portion of the pulse sequence pattern includes:
  causing, based on the selected portion of the pulse sequence pattern, an electron gun of the radiation device to inject electrons into an acceleration structure of the radiation device at an electron frequency;
  causing, based on the selected portion of the pulse sequence pattern, an RF source of the radiation device to inject electromagnetic waves into the acceleration structure at an RF PRF; and
  causing the acceleration structure to deliver, based on the injected electrons and the electromagnetic waves, the one or more radiation pulses to the object.

15. The system of claim 14, wherein a difference between the RF PRF and a prior PF PRF that have been performed by the RF source is less than a threshold.

16. The system of claim 13, wherein the selecting the portion of the pulse sequence pattern based on the time information of the forward window and the determined PRF of the forward window includes:
  determining whether the determined PRF is less than a PRF threshold;
  in response to a determination that the determined PRF is greater than the PRF threshold, selecting a first portion of the pulse sequence pattern, the first portion corresponding to the time information of the forward window and the determined PRF of the forward window; and
  in response to a determination that the determined PRF is less than the PRF threshold, selecting a second portion of the pulse sequence pattern, the second portion corresponding to the time information of the forward window and the PRF threshold.

17. The system of claim 13, wherein the causing the radiation device to deliver the one or more radiation pulses to the object according to the selected portion of the pulse sequence pattern includes:
  determining a first count of radiation pulses based on the target dose and the DPP;
  comparing the first count of pulses to 0 and a second count of pulses in the selected portion of the pulse sequence pattern;
  in response to a determination that the first count of pulses is less than 0, causing the acceleration structure to deliver no pulse to the object;
  in response to a determination that the first count of pulses is larger than the second count of pulses, causing the acceleration structure to deliver the one or more pulses to the object according to the selected portion of the pulse sequence pattern; and
  in response to a determination that the first count of pulses is between 0 and the second count of pulses, causing the acceleration structure to deliver the first count of pulses to the object according to the selected portion of the pulse sequence pattern.

18. The system of claim 13, wherein when executing the set of instructions, the one or more processors are directed to cause the system to perform the operations including:
  determining a dose output rate relating to the forward window based on the DPP and the determined PRF;
  determining whether the dose output rate is in a preset rate range;
  in response to a determination that the dose output rate is in the preset rate range, retaining the determined PRF; and
  in response to a determination that the dose output rate is outside the preset rate range, modifying the determined PRF based on the DPP and the preset range rate of the forward window.

19. The system of claim 13, further comprising an acceleration structure configured to provide radiation pulses delivered to an object;
  an electron gun configured to inject electrons into the acceleration structure;
  a radio frequency (RF) source configured to inject electromagnetic waves into the acceleration structure to accelerate the electrons to generate the radiation pulses; and
  a cooling device configured to maintain at least one component in the system at an operation temperature by circulating a coolant to the at least one component, wherein when executing the set of instructions, the one or more processors are directed to cause the system to perform the operations including:
obtaining one or more parameters of the cooling device that are used to maintain the at least one component at the operation temperature based on a preset range; and
causing the cooling device to operate based on the one or more parameters when the at least one component is working based on an operation parameter that is within in the preset range.

20. A method implemented on a system including one or more processors and one or more storage devices, comprising:
identifying a time window of a procedure;
obtaining operational information of the time window, the operational information including a limit of pulse repetition frequency (PRF) acceleration and a plurality of preliminary radio frequency (RF) pulse repetition frequencies (PRFs);
determining a plurality of updated RF PRFs by updating the plurality of preliminary RF PRFs, a rate of variation between any two adjacent updated RF PRFs being less than or equal to the limit of PRF acceleration; and
causing an RF source to generate electromagnetic waves at the plurality of updated RF PRFs in the time window.

* * * * *